United States Patent [19]

Dolphin et al.

[11] Patent Number: 5,648,485

[45] Date of Patent: Jul. 15, 1997

[54] β, β-DIHYDROXY MESO-SUBSTITUTED CHLORINS, ISOBACTERIOCHLORINS, AND BACTERIOCHLORINS

[75] Inventors: David Dolphin; Christian Brückner, both of Vancouver, Canada

[73] Assignee: University of British Columbia, Vancouver, Canada

[21] Appl. No.: 329,577

[22] Filed: Oct. 26, 1994

[51] Int. Cl.[6] .................................................. C07D 487/22
[52] U.S. Cl. ........................... 540/474; 540/145; 540/472
[58] Field of Search .................................. 540/145, 472, 540/474

[56] References Cited

PUBLICATIONS

Harel et al., "Photoreduction of Porphyrins to Chlorins by Tertiary Amines in the Visible Spectral Range, Optical and EPR Studies", Photochem. and Photobiol., 23:337–41 (1976).

Harel et al., "Photoreduction of Tetraphenylporphyrins by Amines in the Visible Photochemical Syntheses of Reduced Tetraphenylporphyrins and the Mechanism of Photoreduction", J.A.C.S. 11:19, 6228–34 (1978).

Harel et al., "$^{13}$C NMR Studies of Reduced Porphyrin Compounds. Aromatic Delocalization Pathways", Org. Magnetic Resonance, 16:4, 290–95 (1981).

Sternberg et al., "An Overview of Second Generation Drugs for Photodynamic Therapy Including BPD–MA (Benzoporphyrin Derivative)", Photodynamic Therapy and Biomedical Lasers, 470–4 (Spinelli et al. eds. 1992).

Adams et al., "Second Generation Tumour Photosensitisers: The Synthesis and Biological Activity of Octaalkyl Chlorins and Bacteriochlorins with Graded Amphiphilic Character", J. Chem. Soc., Perkin Trans. 1, 1465–70 (1992).

Chang et al., "A Novel Method of Functionalizing the Ethyl Chain of Octaethylporphyrin", J. Org. Chem., 52, 926–29 (1987).

Osuka et al., "Synthesis of 5,15–Diaryl–Substituted Oxochlorins from 5,15–Diaryloctaethylporphyrin", Bull. Chem. Soc. Jap., 66, 3837–39 (1993).

Chang et al., "Migratory Aptitudes in Pinacol Rearrangement of vic–Dihydroxychlorins", J. Heterocyclic Chem., 22, 1739–41 (1985).

Bonnett et al., "The Oxidation of Porphyrins with Hydrogen Peroxide in Sulphuric Acid", Proc. Chem. Soc., 371–72 (1964).

Chang et al., "Differentiation of Bacteriochlorin and Isobacteriochlorin Formation by Metallation. High Yield Synthesis of Porphyrindiones via OsO$_4$ Oxidation", J. Chem. Soc. Chem. Commun., 1213–15 (1986).

Chang et al., "C–Hydroxy–and C–Methylchlorins. A Convenient Route to Heme d and Bonellin Model Compounds", J. Org. Chem., 50, 4989–91 (1985).

Crossley et al., "Tautomerism in 2–Hydroxy–5, 10, 15, 20–tetraphenylporphyrin: An Equilibrium between Enol, Keto and Aromatic Hydroxyl Tautomers", J. Org. Chem., 53, 1132–37 (1988).

Catalano et al., "Efficient Synthesis of 2–Oxy–5, 10, 15, 20–tetraphenylporphyrins from a Nitroporphyrin by a Novel Multi–step Cine–substitution Sequence", J. Chem. Soc., Chem. Comm., 1537–38 (1984).

Berenbaum et al., "meso–Tetra(hydroxyphenyl)porphyrins, a new class of potent tumour photosensitisers with favourable selectivity", Br. J. Cancer, 54, 717–25 (1986).

Ris et al., "Photodynamic Therapy with m–Tetrahydroxyphenylchlorin in vivo: Optimization of the Therapeutic Index", Int. J. Cancer, 55, 245–49 (1993).

Whitlock et al., "Diimide Reduction of Porphyrins", J. Am. Chem. Soc., 91, 7485–89 (1969).

Adams et al. J. Chem. Soc, Perkin Trans 1, 1992 p. 1466.

Primary Examiner—Mukund J. Shah
Assistant Examiner—Pavanaram K. Sripada
Attorney, Agent, or Firm—Morrison & Foerster LLP

[57] ABSTRACT

A β,β'-dihydroxy meso-substituted chlorin, bacteriochlorin or isobacteriochlorin compound having the formula (I) or (II):

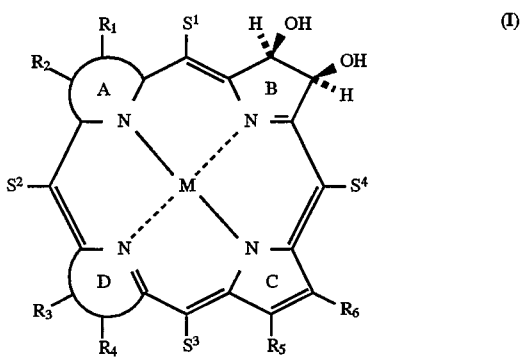

or

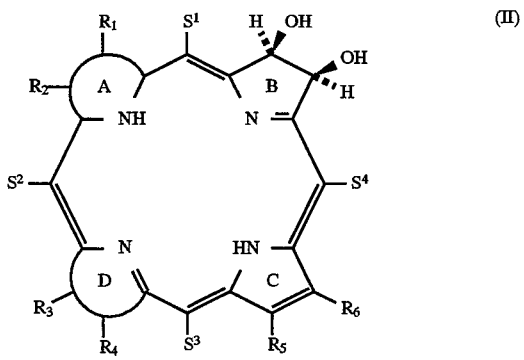

wherein M is a metal. A novel method for synthesizing the compound of formula (I) or (II) comprises the steps of:

a. osmylating a β,β'-unsubstituted, meso-substituted porphyrin to form an osmate ester at the β,β'-position, and b. reducing the osmate ester to form the corresponding β,β'-dihydroxy meso-substituted chlorin, bacteriochlorin or isobacteriochlorin of formula (I) or (II).

12 Claims, 5 Drawing Sheets

β, β-DIHYDROXY MESO-SUBSTITUTED CHLORINS, ISOBACTERIOCHLORINS, AND BACTERIOCHLORINS

FIELD OF THE INVENTION

The present invention relates to certain dihydroxy chlorin, bacteriochlorin or isobacteriochlorin compounds and their preparation. In particular, the invention relates to the dihydroxylation of β,β'-unsubstituted tetrapyrrolic macrocycles that have been substituted in some or all four meso-positions with an alkyl group or an aromatic ring. Many of these compounds are useful photosensitizers in the field of photodynamic therapy ("PDT") for mediating the destruction of unwanted cells or tissues or other undesirable materials by irradiation.

BACKGROUND ART

In the field of PDT, various tetrapyrrolic macrocycles, such as purpurins, chlorins, bacteriochlorins, phthalocyanines and benzochlorins have shown the ability both to localize at a tumor site and to absorb light to form an activated state in response to the light. These macrocycles then exhibit a cytotoxic effect on the cells or other tissues in which they are localized when irradiated at the appropriate wavelength.

To cause the desired phototoxic effect deep within a subject's tissue, however, it is necessary to use photosensitizers that possess high absorption coefficients at wavelengths longer than 650 nm, where body tissues are most transparent to light. See Sternberg et al., "An Overview of Second Generation Drugs for Photodynamic Therapy Including BPD-MA (Benzoporphyrin Derivative)", *Photodynamic Therapy and Biomedical Lasers*, 470–4 (Spinelli et al. eds. 1992).

The reduction of a porphyrin to form a chlorin (i.e., a dihydroporphyrin) changes the optical properties in this desirable way, and reducing the chlorin further to form a bacteriochlorin (i.e., a tetrahydroporphyrin) makes the desired effect even more pronounced. There has only been one general method known to convert meso-tetraphenyl porphyrins into the corresponding chlorins, namely the diimide reduction introduced by Whitlock et al., "Diimide Reduction of Porphyrins", *J. Am. Chem. Soc.*, 91, 7485–89 (1969). However, the product produced does not have a β,β'-dihydroxy substitution pattern.

In addition to the desirable absorptive properties of chlorins and bacteriochlorins, the amphiphilic character of these compounds has been pointed out as being potentially beneficial with respect to the desired biodistribution of the drug. For example, Bonnett et al., "Second Generation Tumour Photosensitisers: The Synthesis and Biological Activity of Octaalkyl Chlorins and Bacteriochlorins with Graded Amphiphilic Character", *J. Chem. Soc., Perkin Trans.* 1, 1465–70 (1992), have suggested that meso-tetra (hydroxyphenyl)chlorins and their corresponding bacteriochlorins could be used as photosensitizers in PDT.

It is known that β-substituted porphyrins can be treated with osmium tetroxide (OsO₄) to oxidize one or more double bonds, thus forming an osmate ester at the β,β'-position, which can then be reduced with any one of a variety of reducing agents to form the corresponding vicinal-diol. For example, in Chang et al., "A Novel Method of Functionalizing the Ethyl Chain of Octaethylporphyrin", *J. Org. Chem.*, 52, 926–29, the corresponding diol was obtained by oxidizing octaethylporphyrin with OsO₄ in the presence of pyridine.

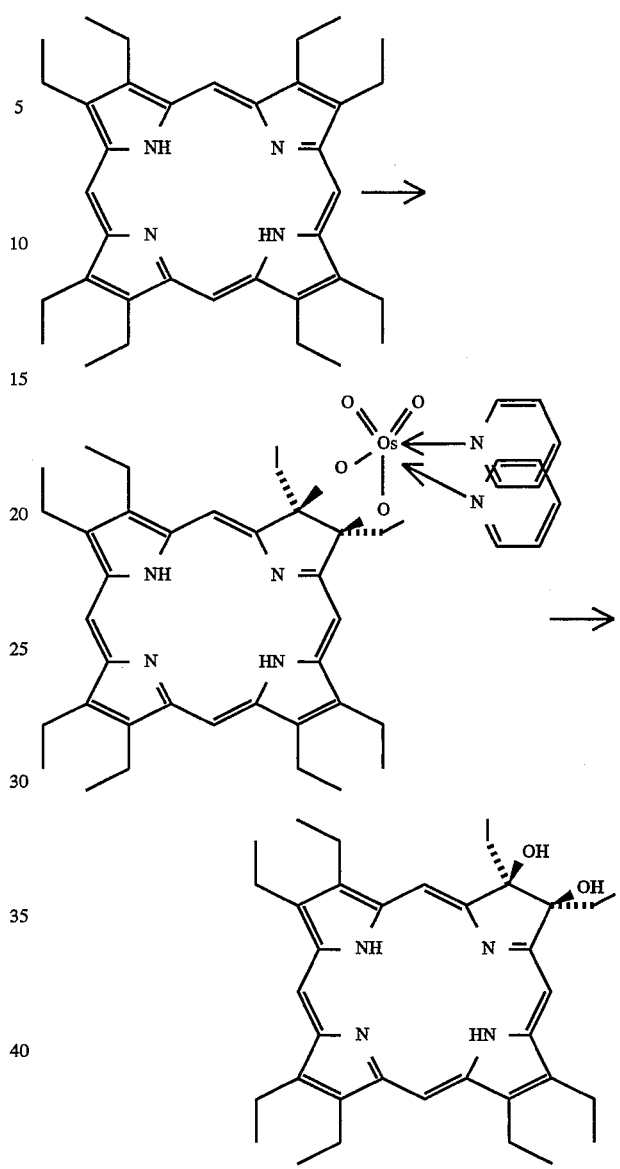

Osmylation of a completely β,β'-alkyl substituted, 5,15-bis-(methylphenyl)porphyrin has similarly produced the corresponding diol. Osuka et al., "Synthesis of 5,15-Diaryl-Substituted Oxochlorins from 5,15-Diaryl-octaethylporphyrin", *Bull. Chem. Soc. Jap.*, 66, 3837–39 (1993).

However, the diols so produced tend to undergo a pinacol-pinacolone-type rearrangement when exposed to acidic conditions, yielding oxochlorins, as shown below:

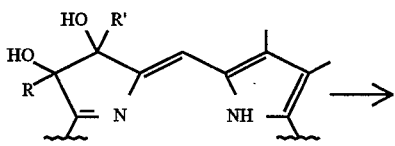

-continued

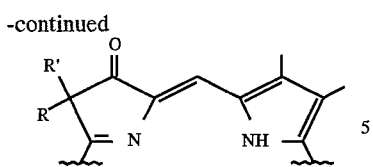

When the migratory aptitude of various substituents was studied, it was established that, from the rearrangement of the β-monoalkyl-substituted diols, hydrogen was the "substituent" with the greatest tendency to migrate in a rearrangement reaction. Chang et al., "Migratory Aptitudes in Pinacol Rearrangement of vic-Dihydroxychlorins", *J. Heterocyclic Chem.*, 22, 1739–41 (1985).

Vicinal-dihydroxychlorins have been obtained from β,β'-alkyl substituted porphyrins by oxidation with osmium tetroxide in pyridine, and it has been confirmed that the product undergoes a pinacol rearrangement on treatment with sulfuric acid. See Bonnett et al., "The Oxidation of Porphyrins with Hydrogen Peroxide in Sulphuric Acid", *Proc. Chem. Soc.*, 371–72 (1964), and Chang et al., "Differentiation of Bacteriochlorin and Isobacteriochlorin Formation by Metallation. High Yield Synthesis of Porphyrindiones via OsO₄ Oxidation", *J. Chem. Soc., Chem. Commun.*, 1213–15 (1986). However, it has not been thought that the dihydroxy osmylation product of a β,β'-unsubstituted, meso-substituted porphyrin would be stable in view of the likelihood of rearrangement.

Further, if the starting porphyrin bears a β-substitution pattern, which lowers the overall symmetry of the molecule, dihydroxylation leads to a non-statistical mixture of stereo- and regioisomers. For example, when the dimethyl ester of deuteroporphyrin-IX is osmylated, a mixture of the following regioisomers and their corresponding stereoisomers is produced. Chang et al., "C-Hydroxy- and C-Methylchlorins. A Convenient Route to Heme d and Bonellin Model Compounds", *J. Org. Chem.*, 50, 4989–91 (1985).

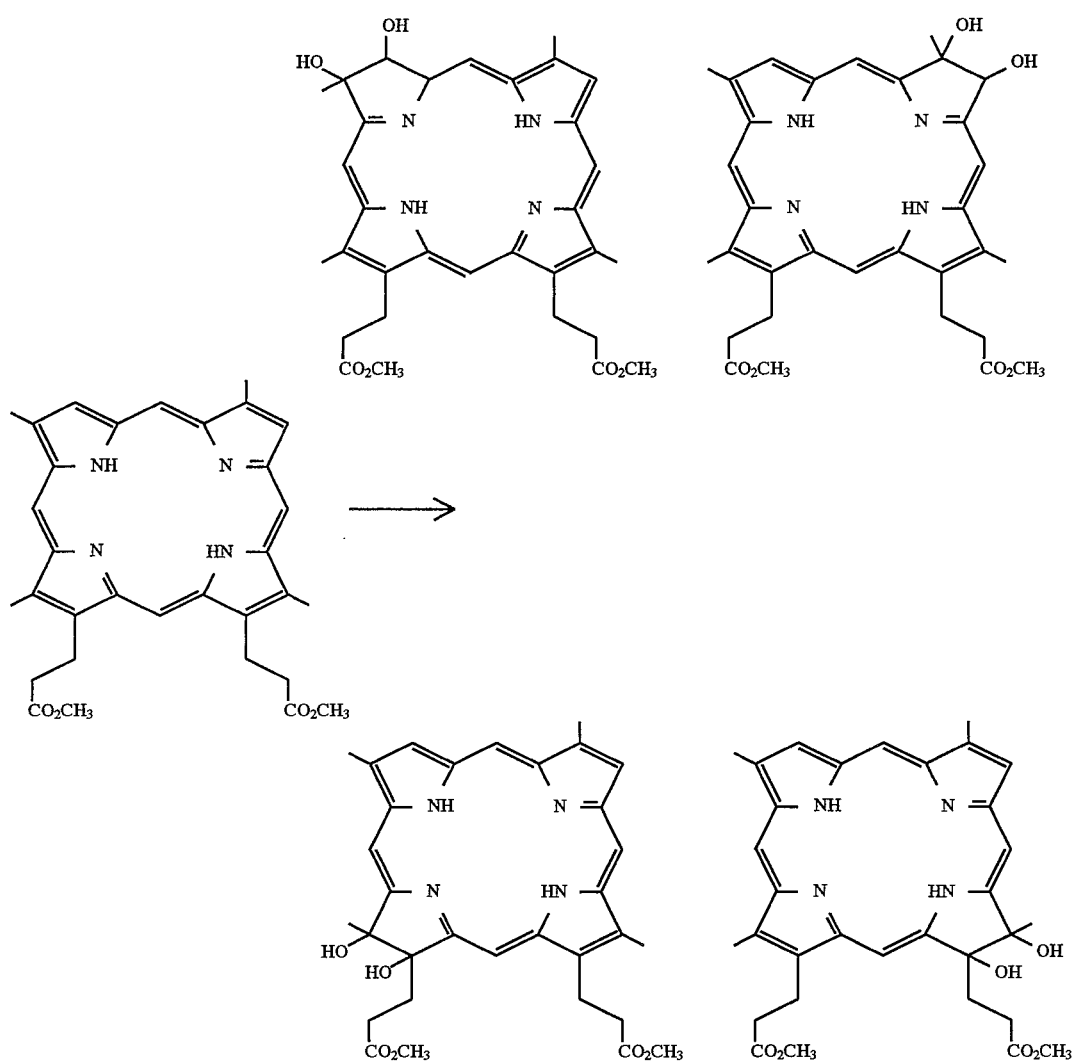

Under the best of conditions, the separation of these regioisomers and stereoisomers is cumbersome.

It has now been found that β,β'-unsubstituted, meso-substituted porphyrin compounds can be β,β'-dihydroxylated via the addition of OsO₄, followed by reduction to give the vic-diol, as shown below:

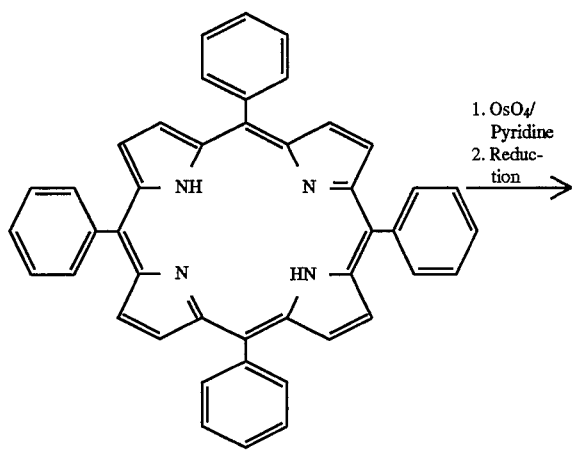

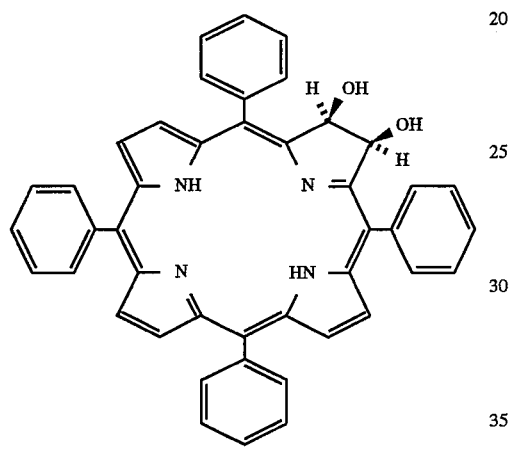

The resulting meso-substituted vic-diols are unexpectedly stable. Surprisingly, dehydration and rearrangement only takes place under relatively harsh conditions, such as treatment with refluxing benzene containing catalytic amounts of $HClO_4$. This is unexpected in view of, not only the high migratory aptitude of the β-hydrogens, but also the expected tendency of the molecule to eliminate water, thus reconstituting a fully conjugated, porphyrin resonance structure as the enolic tautomer, as shown below. Crossley et al., "Tautomerism in 2-Hydroxy-5,10,15,20-tetraphenylporphyrin: An Equilibrium Between Enol, Keto, and Aromatic Hydroxyl Tautomers", *J. Org. Chem.*, 53, 1132–37 (1988).

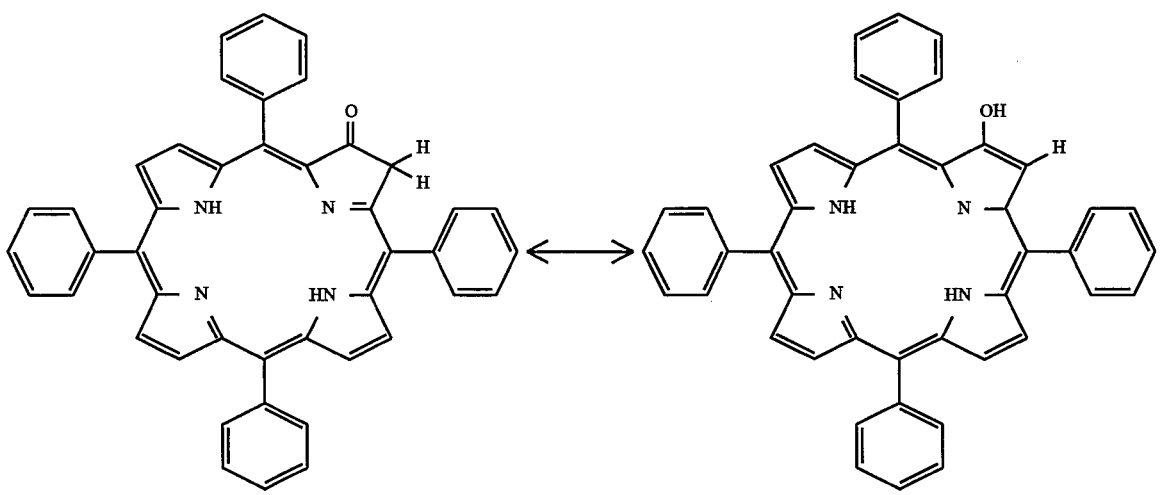

Such meso-phenyl oxoporphyrins have been previously prepared via a fundamentally different route. See, e.g., Catalano et al., "Efficient Synthesis of 2-Oxy-5,10,15,20-tetraphenylporphyrins from a nitroporphyrin by a Novel Multi-Step Cine-substitution Sequence", *J. Chem. Soc., Chem. Comm.*, 1537–38 (1984).

It has been found that, when hydroxy groups are added to a pre-existing meso-substituent, for example, the phenyl substituents in meso-tetra(hydroxyphenyl)-porphyrins, chlorins and bacteriochlorins can be effective as active PDT agents. See Berenbaum et al., "Meso-Tetra(hydroxyphenyl)-porphyrins, a New Class of Potent Tumour Photosensitisers with Favourable Selectivity," *Br. J. Cancer*, 54, 717–25 (1986) and Ris et al., "Photodynamic Therapy with m-Tetrahydroxyphenylchlorin in vivo: Optimization of the Therapeutic Index", *Int. J. Cancer*, 55, 245–49 (1993). By introducing hydroxy-functionalities into the β-positions, not only has a new class of photosensitizer compounds been found, but there is reason to believe that the photosensitizers of the invention are even superior to known compounds due to enhancement of amphiphilicity of the molecule.

Further, upon β,β'-dihydroxylation, the high symmetry of the starting materials causes the formation of only one regio- and stereoisomer of the resulting chlorin. For example, the dihydroxylation of meso-tetraphenylporphyrin generates only one isomer of β,β'-dihydroxy-meso-tetraphenylbacteriochlorin. Further still, subsequent β,β'-dihydroxylation of the β,β'-hydroxychlorin generates only two, easily separable diastereomers of the tetrahydroxybacteriochlorin product. This significant reduction of isomers provides a method for obtaining PDT agents in high yields, which is of great practical, economical and medicinal importance.

Consistent with previous observations (see, e.g., Whitlock et al, "Diimide Reduction of Porphyrins" *J. Am. Chem. Soc.*, 91, 7485–89 (1969) and Chang et al. "Differentiation of Bacteriochlorin and Isobacteriochlorin Formation by Metallation: High Yield Synthesis of Porphyrindiones via OsO$_4$ Oxidation", *J. Chem. Soc., Chem. Comm.*, 1213–15 (1986)), the β-hydroxylation of β,β'-dihydroxychlorins (and the diimide reduction β,β'-dihydroxychlorins or, for that matter, the β,β'-dihydroxylation of tetraphenylchlorins) are susceptible to a pronounced metal-directing effect. Osmylation/reduction of metallochlorins produces a metallo-isobacteriochlorin chromophore, from which the parent isobacteriochlorin chromophore can be obtained by demetallation. In contrast, osmylation/reduction of the free base chlorins produces the corresponding bacteriochlorin chromophores.

Yet another advantage is that the meso-substituent can be widely derivatized, particularly when it is an aryl ring, such as a phenyl group. Thus, by hydroxylating β,β'-unsubstituted, meso-substituted porphyrins and chlorins via oxidation with OsO$_4$, followed by reduction of the intermediate osmate ester formed at the β,β'-position, there can be made a number of related vic-diol substituted chlorins and bacteriochlorins exhibiting particularly desirable characteristics as PDT agents, such as intensified and bathochromically shifted Q bands and increased amphiphilicity. Moreover, due to the ability to further derivatize the meso-substituents themselves, an opportunity is provided for fine-tuning the pharmacokinetics and -dynamics of the compounds to an even greater degree.

DISCLOSURE OF THE INVENTION

According to the present invention, there have been prepared novel β,β'-dihydroxy meso-substituted chlorin, isobacteriochlorin and bacteriochlorin compounds having the formula (I) or (II):

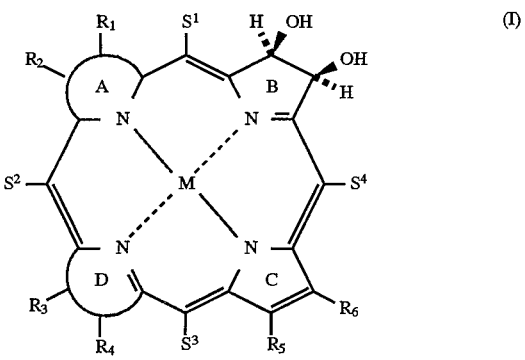

or

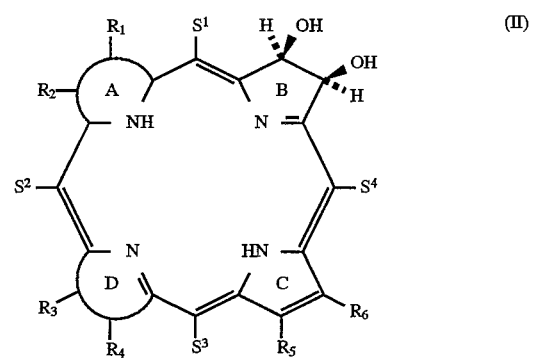

wherein M is a metal selected from the group consisting of Ni(II), Cu(II), Zn(II), Fe(III)Cl, Sn, Ge, Si, Ga, Al, Mn(III), Gd(III), In and Tc;

A is a ring having the structure:

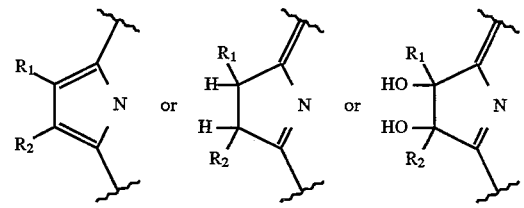

D is a ring having the structure:

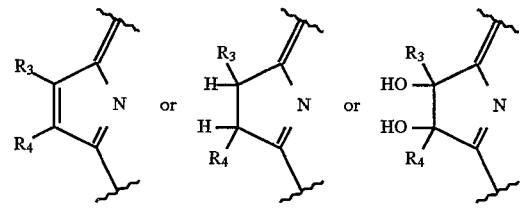

$R_1$ through $R_6$ are independently a hydrogen atom, a lower alkyl group, a lower alkyl carboxylic acid or acid ester group, keto, hydroxy, nitro, amino or a group that, taken together with another ring, ring substituent or meso-substituent, forms a fused 5- or 6-membered ring; and $S^1$ through $S^4$ are H, substituted or unsubstituted alkyl groups, or substituted or unsubstituted aromatic rings, which may be the same or different, with the proviso that at least one of $S^1$ through $S^4$ is not H.

Further, a method has been found for efficiently synthesizing the compounds of formulas (I) and (II). Specifically, in the invention, a method for making a compound having formula (I) comprises the steps of:

a. osmylating a meso-substituted metalloporphyrin having the formula (III):

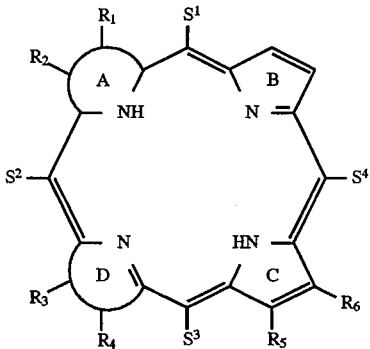

(III)

where A, D, R₁ through R₆ and S¹ through S⁴ are described above, to form an osmate ester at the β,β'-position; and b. reducing the osmate ester to form the corresponding β,β'-dihydroxy meso-substituted chlorin, bacteriochlorin or isobacteriochlorin of formula (I).

Three methods of making the demetallated compounds of formula (II) are disclosed. The first comprises the steps of:

a. osmylating a meso-substituted metalloporphyrin having the formula (III) to form an osmate ester at the β,β'-position;

b. reducing the osmate ester to form the corresponding β,β'-dihydroxy meso-substituted chlorin, bacteriochlorin or isobacteriochlorin of formula (I); and c. demetallating the β,β'-dihydroxy meso-substituted chlorin, bacteriochlorin or isobacteriochlorin of formula (I) after the reducing step to form the demetallated β,β'-dihydroxy meso-substituted chlorin, bacteriochlorin or isobacteriochlorin of formula (II).

The second method of making a demetallated compound of formula (II) comprises the steps of:

a. osmylating a meso-substituted metalloporphyrin having the formula (III) to form an osmate ester at the β,β'-position; and b. demetallating the osmate ester; and c. reducing the demetallated osmate ester to form the corresponding β,β'-dihydroxy meso-substituted chlorin or bacteriochlorin compound of formula (II).

Yet a third method of making a demetallated compound of formula (II) comprises the steps of:

a. osmylating a meso-substituted porphyrinogenic compound having the formula (IV)

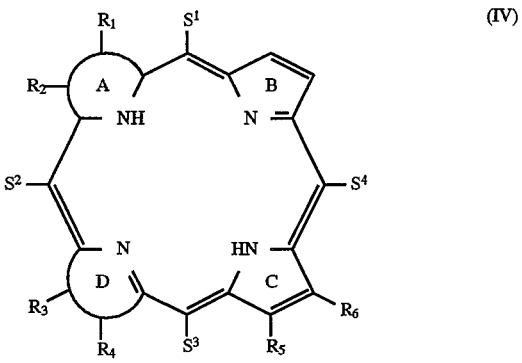

(IV)

where A, D, R₁ through R₆ S¹ through S⁴ are as described above, to form an osmate ester at the β,β'-position; and b. reducing the osmate ester to form the corresponding β,β'-dihydroxy meso-substituted chlorin or bacteriochlorin compound of formula (II).

BRIEF DESCRIPTION OF DRAWINGS

The present invention will be more clearly understood by referring to the following drawings, in which.

MODES OF CARRYING OUT THE INVENTION

Figure 1:
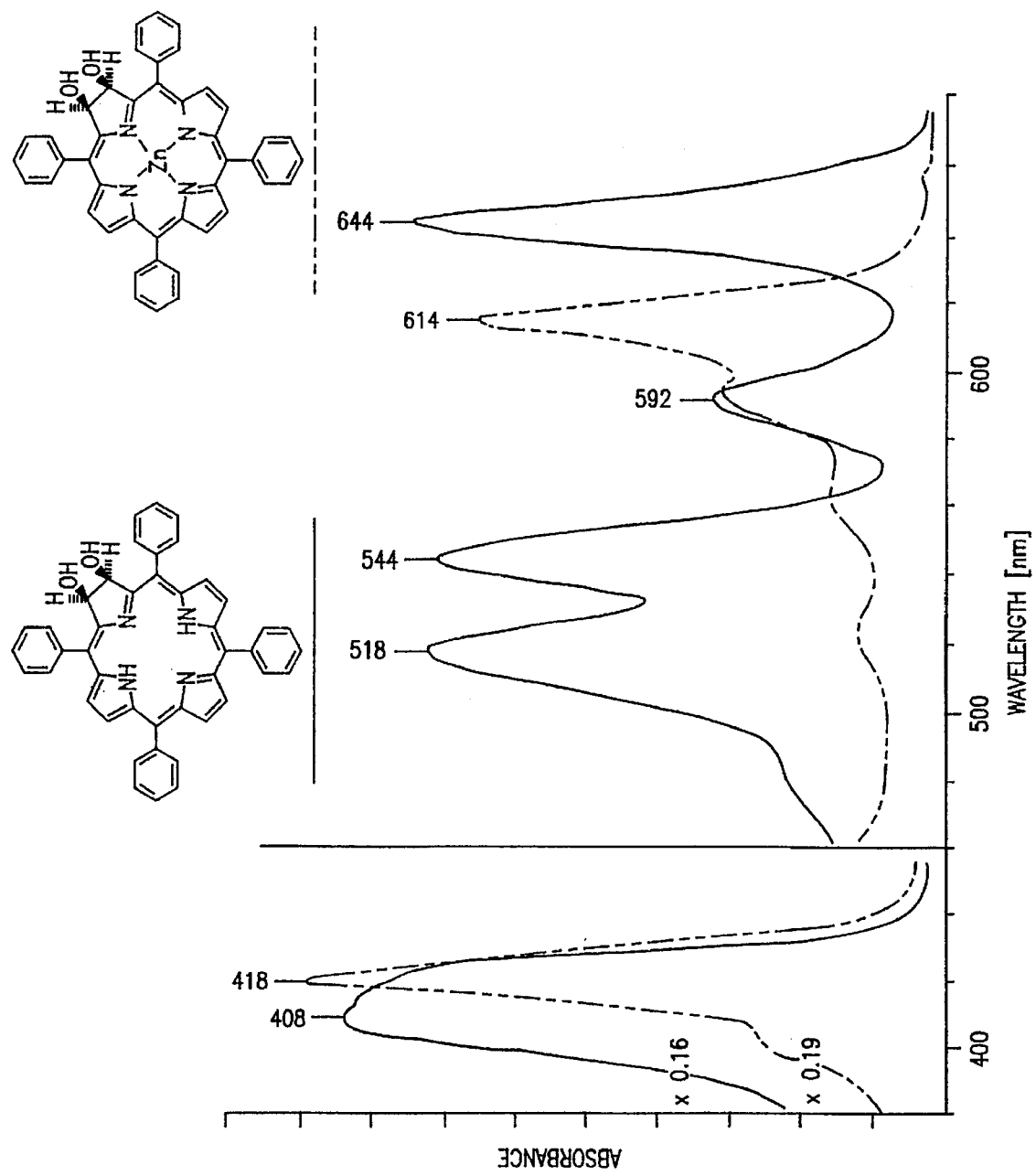
FIG. 1 shows the UV-Vis spectrum of 2,3-vic-dihydroxy-tetraphenylchlorin (solid line) and the UV-Vis spectrum of [2,3-vic-dihydroxy-tetraphenylchlorinato] zinc (II) (broken line).
Figure 2:
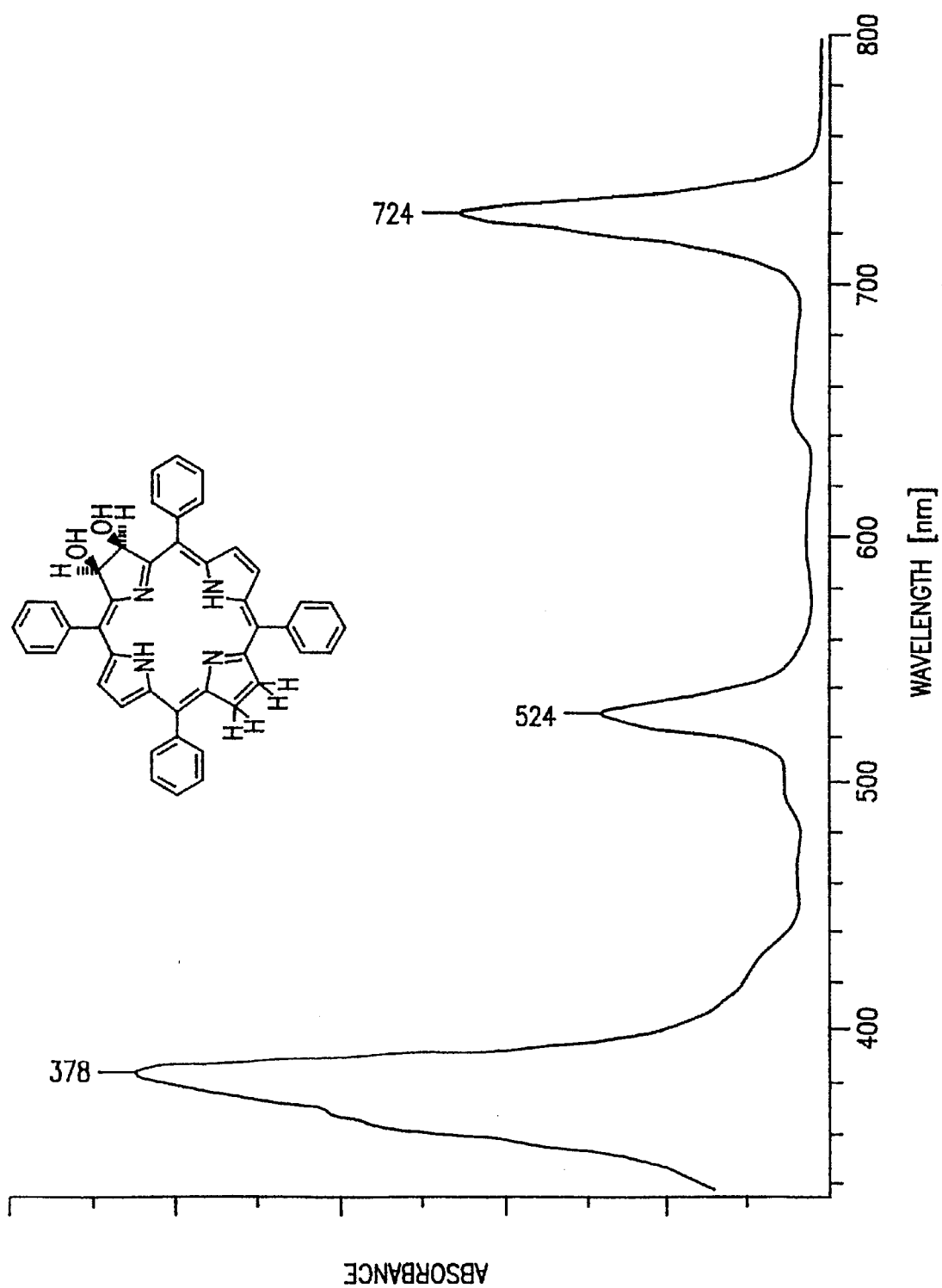
FIG. 2 shows the UV-Vis spectrum of 2,3-vic-dihydroxy-tetraphenylbacteriochlorin.
Figure 3:
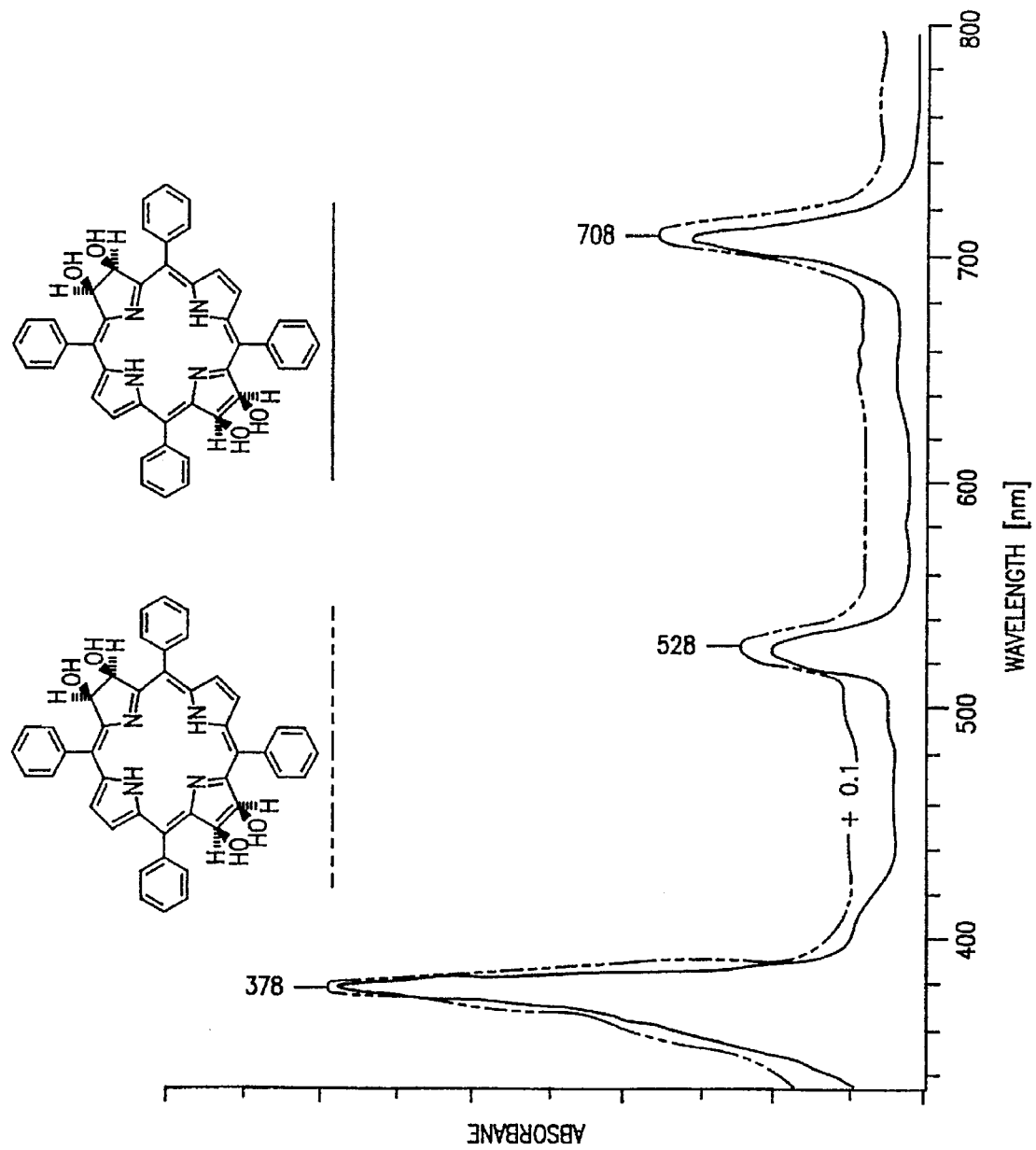
FIG. 3 shows the UV-Vis spectrum of 2,3,12,13-tetrahydroxy-tetraphenylbacteriochlorin-E-isomer (solid line) and the UV-Vis spectrum of 2,3,12,13-tetrahydroxy-tetraphenylbacteriochlorin-Z-isomer (broken line).
Figure 4:
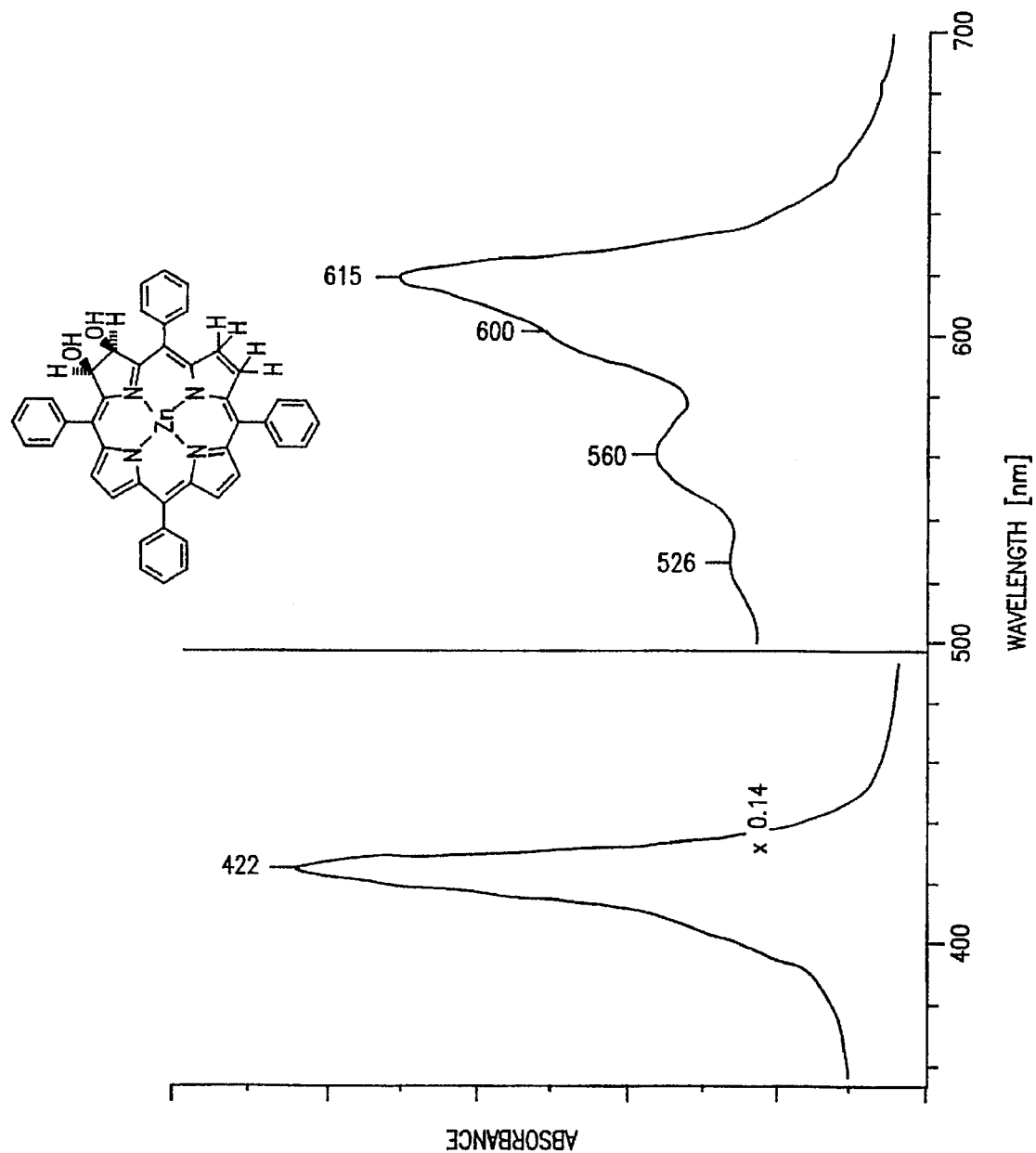
FIG. 4 shows the UV-Vis spectrum of [7,8-vic-dihydroxy-tetraphenylisobacteriochlorinato]zinc(II).
Figure 5:
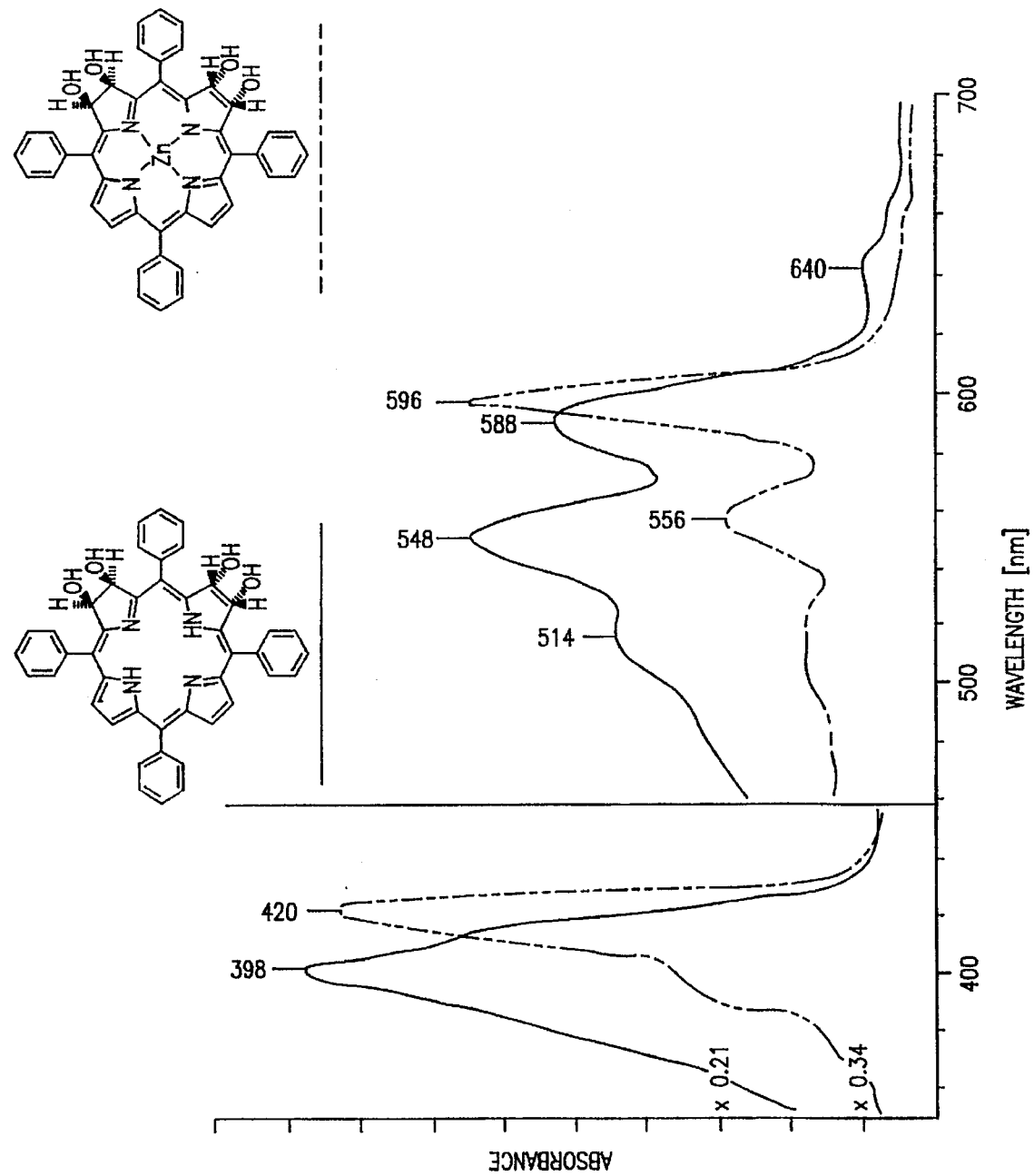
FIG. 5 shows the UV-Vis spectrum of 2,3,7,8-tetrahydroxy-tetraphenylisobacteriochlorin-E-isomer (solid line) and [2,3,7,8-tetrahydroxy-tetraphenylisobacteriochlorinato]zinc(II)-E-isomer (broken line).

The β,β'-dihydroxy meso-substituted chlorin, bacteriochlorin or isobacteriochlorin compounds of the invention have formula (I) or formula (II), as described and shown above. M in formula (I) can be any metal species that is capable of forming the complex of formula (I), but is preferably selected from the group consisting of Ni(II), Cu(II), Zn, Sn, Ge, Si, Ga and Al. An important characteristic of the metal selected is that it should be possible to introduce the metal into the porphyrin structure and then also possible to remove it from the chlorin resulting from the process of the invention.

A can be any ring having the structure:

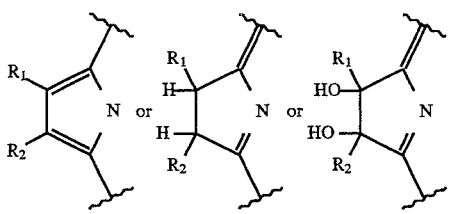

D can be any ring having the structure:

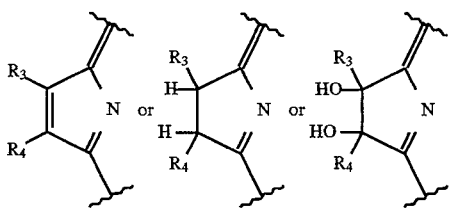

It should be understood that all corresponding resonance forms of the above structures are also intended to be covered by the terms "A" and "D". Preferably, however, at least one of the rings A and D is identical to the rings B and C. Even more preferably, both rings A and D are identical to the other rings B and C and, with them, form a porphyrin core structure having four such rings, each ring being connected by a bridging carbon atom that is referred to as the meso-position.

$R_1$ through $R_6$ can be any one of a large number of ring substituents, so long as they do not interfere with the osmylation and reduction steps outlined above. Preferably, $R_1$ through $R_6$ are independently a hydrogen atom; a lower alkyl group, such as methyl, ethyl, n-propyl, isopropyl, t-butyl and n-pentyl; a lower alkyl carboxylic acid, such as formyl, carboxymethyl, carboxyethyl, carboxy-n-butyl, carboxy-sec-butyl, carboxy-n-hexyl; a carboxylic acid ester group, such as $-CH_2CH_2COOCH_3$, $-CH_2CH_2COOCH_2CH_3$, $-CH_2CH(CH_3)COOCH_2CH_3$, $-CH_2CH_2CH_2COOCH_2CH_2CH_3$, $-CH_2CH(CH_3)_2COOCH_2CH_3$; keto; hydroxy; nitro; amino; or the like.

Further, $R_1$ and $R_2$, $R_3$ and $R_4$, or $R_5$ and $R_6$, can be taken together with another ring, ring substituent or meso-substituent to form a fused 5- or 6-membered ring. The fused 5- or 6-membered ring so formed may be any saturated or unsaturated, carbocyclic or heterocyclic 5- or 6-membered ring that does not interfere with the osmylation and reduction reaction steps of the invention. Examples of such rings include cyclopentane, furan, thiophene, pyrrole, isopyrrole, 3-isopyrrole pyrazole, 2-isoimidazole, 1,2,3-triazole, 1,2,4-triazole, 1,2-dithiole, 1,3-dithiole, 1,2,3-oxathiole, isoxazole, oxazole, thiazole, isothiazole, 1,2,3-oxadiathiazole, 1,2,4-oxadiazole, 1,2,5-oxadiazole, 1,3,4-oxadiazole, 1,2,3-dioxazole, 1,2,4-dioxazole, 1,2,5-oxathiazole, 1,3-oxathiole, benzene, cyclohexane, 1,2-pyran, 1,4-pyran, 1,2-pyrone, 1,4-pyrone, 1,2-dioxin, 1,3-dioxin (dihydro form), pyridine, pyridazine, pyrimidine, pyrazine, piperazine, 1,3,5-triazine, 1,2,4-triazine, 1,2,4-oxazine, 1,3,2-oxazine, o-isoxazine, 1,2,5-oxathiazine, 1,4-oxazine, p-isoxazine, 1,2,6-oxathiazine, 1,3,5,2-oxadiazine, morpholine, azepine, oxepin, thiepin, 1,2,4-diazepine, and the like. Preferably, when $R_1$ and $R_2$, $R_3$ and $R_4$, or $R_5$ and $R_6$, form a fused, 5- to 6-membered ring, the ring is a 6-membered ring. Most preferably, when $R_1$ and $R_2$, $R_3$ and $R_4$, or $R_5$ and $R_6$, form a ring, it is a 6-membered carbocyclic ring, i.e., a benzene ring.

In a particularly preferred embodiment, $R_1$ through $R_6$ are independently hydrogen, methyl, ethyl, or lower alkyl esters, most preferably being hydrogen, methyl or ethyl.

$S^1$ through $S^4$ are the same or different and can be H, any one of a large number of substituted or unsubstituted alkyl groups, substituted or unsubstituted cycloalkyl groups, and aromatic rings. When one or more of $S^1$ through $S^4$ is an alkyl group, they preferably have from about 1 to about 18 carbon atoms, more preferably about 1 to 12 carbon atoms and, even more preferably, about 1–6 carbon atoms. Examples of typical alkyl groups are methyl, ethyl, isopropyl, sec-butyl, tert-butyl, n-pentyl and n-octyl.

When one or more of $S^1$ through $S^4$ is an alkyl group, it may be unsubstituted or substituted with any group that does not interfere with the osmylation or reduction reactions. For example, when one or more of $S^1$ through $S^4$ is an alkyl group may be substituted by a halogen atom, such as fluorine, chlorine or bromine; a hydroxy group, such as in pentoses and hexoses; thiol; or a carbonyl group, such as when the alkyl group is an aldehyde, ketone, carboxylic acid (e.g., a fatty acid) or ester or amide; a primary, secondary, tertiary, or quaternary amino group; nitrile; a phosphate group; a sulfonate group; and the like.

When one or more of $S^1$ through $S^4$ is a cycloalkyl group, it preferably contains from about 3 to about 7 carbon atoms. Examples of typical cycloalkyl groups include cyclopropyl, cyclohexyl, and cycloheteroalkyl, such as glucopyranose or fructofuranose sugars. When one or more of $S^1$ through $S^4$ is a cycloalkyl group, it may be unsubstituted or substituted with any group that does not interfere with the osmylation or reduction reactions. For example, when one or more of $S^1$ through $S^4$ is a cycloalkyl group, they may be substituted by any of the same substituents described above for the case when one or more of $S^1$ through $S^4$ is an alkyl group.

When one or more of $S^1$ through $S^4$ is an aryl group, it preferably contains from about 5 to about 12 carbon atoms, optionally containing one or more heteroatoms, and optionally including rings that are fused to the existing conjugated porphyrin ring structure. Examples of suitable aromatic rings include furan, thiophene, pyrrole, isopyrrole, 3-isopyrrole, pyrazole, 2-isoimidazole, 1,2,3-triazole, 1,2,4-triazole, 1,2-dithiole, 1,3-dithiole, 1,2,3-oxathiole, isoxazole, oxazole, thiazole, isothiazole, 1,2,3-oxadiazole, 1,2,4-oxadiazole, 1,2,5-oxadiazole, 1,3,4-oxadiazole, 1,2,3,4-oxatriazole, 1,2,3,5-oxatriazole, 1,2,3-dioxazole, 1,2,4-dioxazole, 1,3,2-dioxazole, 1,3,4-dioxazole, 1,2,5-oxathiazole, 1,3-oxathiole, benzene, 1,2-pyran, 1,4-pyran, 1,2-pyrone, 1,4-pyrone, 1,2-dioxin, 1,3-dioxin, pyridine, N-alkyl pyridinium, pyridazine, pyrimidine, pyrazine, 1,3,5-triazone, 1,2,4-triazine, 1,2,3-triazine, 1,2,4-oxazine, 1,3,2-oxazine, 1,3,6-oxazine, 1,4-oxazine, o-isoxazine, p-isoxazine, 1,2,5-oxathiazine, 1,4-oxazine, o-isoxazine, p-isoxazine, 1,2,5-oxathiazine, 1,2,6-oxathiazine, 1,4,2-oxadiazine, 1,3,5,2-oxadiazine, azepine, oxepin, thiepin, 1,2,4-diazepine, indene, isoindene, benzofuran, isobenzofuran, thionaphthene, isothionaphthene, indole, indolenine, 2-isobenzazole, 1,4-pyrindine, pyrando[3,4-b]-pyrrole, isoindazole, indoxazine, benzoxazole, anthranil, naphthalene, 1,2-benzopyran, 1,2-benzopyrone, 1,4-benzopyrone, 2,1-benzopyrone, 2,3-benzopyrone, quinoline, isoquinoline, 1,2-benzodiazine, 1,3-benzodianzine, naphthyridine, pyrido[3,4-b]-pyridine, pyrido[3,2-b]-pyridine, pyrido[4,3-b]-pyridine, 1,3,2-benzoxazine, 1,4,2-benzoxazine, 2,3,1-benzoxazine, 3,1,4-benzoxazine, 1,2-benzisoxazine, 1,4-benzisoxazine, anthracene, phenanthrene, carbazole, xanthene, acridine, purine, steroidal compounds and the like.

In a particularly preferred embodiment, $S^1$ through $S^4$ are selected from the group consisting of phenyl, naphthyl, pyridinyl, and lower N-alkyl pyridinium salts. Even more preferably, $S^1$ through $S^4$ are identical.

In another embodiment, at least one of $S^1$ through $S^4$ has the structure:

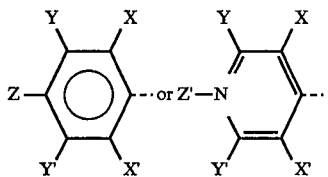

wherein X, Y, Z, X', Y' and Z' can be any one of a large number of substituents and are generally used to "fine tune" the biological activity, the biodistribution, the absorption and clearance characteristics, and the physical properties of the desired product. One way in which this may be done by selecting substituents in such a manner that the compound of formula (I) or (II) is an amphiphilic molecule. By "amphiphilic" is meant the molecule becomes more asymmetric, such as (1) having both (a) a highly polar, water-soluble region and (b) a highly hydrophobic, water-insoluble region; or (2) having both (a) a nonionic region and (b) an ionic region.

However, it should be noted that the invention also includes $\beta,\beta'$-dihydroxy meso-substituted chlorin, bacteriochlorin or isobacteriochlorin compounds having substantially or exactly identical aryl substituents. Further, any aryl substituent chosen should also have no adverse effect on the ability of the compound to undergo the step "a." and step "b." reactions used to prepare the compounds of the invention.

Preferably, X, X', Y, Y' and Z are independently (1) hydrogen; (2) halogen, such as fluoro, chloro, iodo and bromo; (3) lower alkyl, such as methyl, ethyl, n-propyl, isopropyl, t-butyl, n-pentyl and the like groups; (4) lower alkoxy, such as methoxy, ethoxy, isopropoxy, n-butoxy, t-pentoxy and the like; (5) hydroxy; (6) carboxylic acid or acid salt, such as —$CH_2COOH$, —$CH_2COO\text{-}Na^+$, —$CH_2CH(Br)COOH$, —$CH_2CH(CH_3)COOH$, —$CH(Cl)$-$CH_2$-$CH(CH_3)$-$COOH$, —$CH_2$-$CH_2$-$C(CH_3)_2$-$COOH$, —$CH_2$-$CH_2$-$C(CH_3)_2$-$COO^-K^+$, —$CH_2$-$CH_2$-$CH_2$-$CH_2$-$COOH$, $C(CH_3)_3$-$COOH$, $CH(Cl)_2$-$COOH$ and the like; (7) carboxylic acid ester, such as —$CH_2CH_2COOCH_3$, —$CH_2CH_2COOCH_2CH_3$, —$CH_2CH(CH_3)COOCH_2CH_3$, —$CH_2CH_2CH_2COOCH_2CH_3$, —$CH_2CH(CH_3)_2COOCH_2CH_3$, and the like; (8) sulfonic acid or acid salt, for example, group I and group II salts, ammonium salts, and organic cation salts such as alkyl and quaternary ammonium salts; (9) sulfonic acid ester, such as methyl sulfonate, ethyl sulfonate, cyclohexyl sulfonate and the like; (10) amino, such as unsubstituted primary amino, methylamino, ethylamino, n-propylamino, isopropylamino, 5-butylamino, sec-butylamino, dimethylamino, trimethylamino, diethylamino, triethylamino, di-n-propylamino, methylethylamino, dimethyl-sec-butylamino, 2-aminoethanoxy, ethylenediamino, 2-(N-methylamino) heptyl, cyclohexylamino, benzylamino, phenylethylamino, anilino, N-methylanilino, N,N-dimethylanilino, N-methyl-N-ethylanilino, 3,5-dibromo-4-anilino, p-toluidino, diphenylamino, 4,4'-dinitrodiphenylamino and the like; (11) cyano; (12) nitro; (13) a biologically active group; or (14) any other substituent that increases the amphiphilic nature of the compound of formula (I) or (II).

The term "biologically active group" can be any group that selectively promotes the accumulation, elimination, binding rate, or tightness of binding in a particular biological environment. For example, one category of biologically active groups is the substituents derived from sugars, specifically, (1) aldoses such as glyceraldehyde, erythrose, threose, ribose, arabinose, xylose, lyxose, allose, altrose, glucose, mannose, gulose, idose, galactose, and talose; (2) ketoses such as hydroxyacetone, erythrulose, rebulose, xylulose, psicose, fructose, sorbose, and tagatose; (3) pyranoses such as glucopyranose; (4) furanoses such as fructofuranose; (5) O-acyl derivatives such as penta-O-acetyl-$\alpha$-glucose; (6) O-methyl derivatives such as methyl $\alpha$-glucoside, methyl $\beta$-glucoside, methyl $\alpha$-glucopyranoside, and methyl-2,3,4,6-tetra-O-methyl-glucopyranoside; (7) phenylosazones such as glucose phenylosazone; (8) sugar alcohols such as sorbitol, mannitol, glycerol, and myo-inositol; (9) sugar acids such as gluconic acid, glucaric acid and glucuronic acid, $\delta$-gluconolactone, $\delta$-glucuronolactone, ascorbic acid, and dehydroascorbic acid; (10) phosphoric acid esters such as $\alpha$-glucose 1-phosphoric acid, $\alpha$-glucose 6-phosphoric acid, $\alpha$-fructose 1,6-diphosphoric acid, and $\alpha$-fructose 6-phosphoric acid; (11) deoxy sugars such as 2-deoxy-ribose, rhamnose (deoxymannose), and fucose (6-deoxy-galactose); (12) amino sugars such as glucosamine and galactosamine; muramic acid and neuraminic acid; (13) disaccharides such as maltose, sucrose and trehalose; (14) trisaccharides such as raffinose (fructose, glucose, galactose) and melezitose (glucose, fructose, glucose); (15) polysaccharides (glycans) such as glucans and mannans; and (16) storage polysaccharides such as $\alpha$-amylose, amylopectin, dextrins, and dextrans.

Amino acid derivatives are also useful biologically active substituents, such as those derived from valine, leucine, isoleucine, threonine, methionine, phenylalanine, tryptophan, alanine, arginine, aspartic acid, cystine, cysteine, glutamic acid, glycine, histidine, proline, serine, tyrosine, asparagine and glutamine. Also useful are peptides, particularly those known to have affinity for specific receptors, for example, oxytocin, vasopressin, bradykinin, LHRH, thrombin and the like.

Another useful group of biologically active substituents are those derived from nucleosides, for example, ribonucleosides such as adenosine, guanosine, cytidine, and uridine; and 2'-deoxyribonucleosides, such as 2'-deoxyadenosine, 2'-deoxyguanosine, 2'-deoxycytidine, and 2'-deoxythymidine.

Another category of biologically active groups that is particularly useful is any ligand that is specific for a particular biological receptor. The term "ligand specific for a receptor" refers to a moiety that binds a receptor at cell surfaces, and thus contains contours and charge patterns that are complementary to those of the biological receptor. The ligand is not the receptor itself, but a substance complementary to it. It is well understood that a wide variety of cell types have specific receptors designed to bind hormones, growth factors, or neurotransmitters. However, while these embodiments of ligands specific for receptors are known and understood, the phrase "ligand specific for a receptor", as used herein, refers to any substance, natural or synthetic, that binds specifically to a receptor.

Examples of such ligands include: (1) the steroid hormones, such as progesterone, estrogens, androgens, and the adrenal cortical hormones; (2) growth factors, such as epidermal growth factor, nerve growth factor, fibroblast growth factor, and the like; (3) other protein hormones, such as human growth hormone, parathyroid hormone, and the like; and (4) neurotransmitters, such as acetylcholine, serotonin, dopamine, and the like. Any analog of these substances that also succeeds in binding to a biological receptor is also included.

Particularly useful examples of substituents tending to increase the amphiphilic nature of the compound of formula (I) include: (1) long chain alcohols, for example, —$C_{12}H_{24}$-OH where —$C_{12}H_{24}$ is hydrophobic; (2) fatty acids and their salts, such as the sodium salt of the long-chain fatty acid oleic acid; (3) phosphoglycerides, such as phosphatidic acid, phosphatidyl ethanolamine, phosphatidyl choline, phosphatidyl serine, phosphatidyl inositol, phosphatidyl glycerol, phosphatidyl 3'-O-alanyl glycerol, cardiolipin, or phosphatidal choline; (4) sphingolipids, such as sphingomyelin; and (5) glycolipids, such as glycosyldiacylglycerols, cerebrosides, sulfate esters of cerebrosides or gangliosides.

In a preferred embodiment, X, X', Y, Y' and Z are independently hydrogen, halogen, lower alkyl, lower alkoxy, hydroxy, carboxylic acid or acid salt, carboxylic acid ester, sulfonic acid or acid salt, sulfonic acid ester, substituted or unsubstituted amino, cyano, nitro, or a biologically active group, and Z' is hydrogen or lower alkyl. In another embodiment, X, Y, X' and Y' are each hydrogen, and Z is selected from the group consisting of hydrogen, halogen, lower alkyl, lower alkoxy, hydroxy, carboxylic acid, carboxylic acid ester, sulfonic acid ester (especially aromatic sulfonic acid ester), nitro, amino (especially lower alkyl amino), cyano, and a biologically active group.

In yet another embodiment, X, Y, Z, X' and Y' are selected from the group consisting of hydrogen, methyl, ethyl, t-butyl, methoxy, hydroxy, OR where R is an alkyl group or a fatty acid group having from 6 to 18 carbon atoms, fluoro, chloro, iodo, bromo, —C(O)-OCH$_3$, cyano, nitro, or a ligand specific for a biological receptor. In a further preferred embodiment, X, X', Y and Y' and Z is selected from the group consisting of hydrogen, halogen, lower alkyl, lower alkoxy, hydroxy, carboxylic acid or acid salt, carboxylic acid ester, sulfonic acid ester, sulfonic acid or acid salt, nitro, amino, cyano, and a biologically active group. In still another preferred embodiment, at least one of X, Y, Z, X' and Y' is a biologically active group or a substituent that increases the amphiphilic nature of the molecule.

Particularly preferred specific examples of groups that can serve as one or more of $S^1$ through $S^4$ include the following:

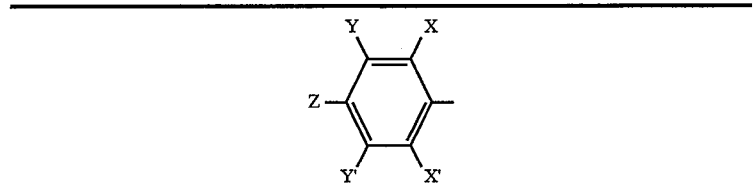

| X | X' | Y | Y' | Z |
|---|---|---|---|---|
| —H | —H | —H | —H | —H |
| —OH | —H | —H | —H | —H |
| —H | —H | —OH | —H | —H |
| —H | —H | —H | —H | —OH |
| —H | —H | —OH | —OH | —OH |
| —H | —H | —H | —H | —SO$_3$H(Na) |
| —CH$_3$ | —CH$_3$ | —H | —H | —CN |
| —H | —H | —OCH$_3$ | —OCH$_3$ | —OCH$_3$ |
| —H | —H | —H | —H | —COOH(Na) |
| —H | —H | —COOH(Na) | —COOH(Na) | —H |
| —H | —H | —H | —H | —C$_6$H$_{12}$COOH(Na) |
| —H | —H | —H | —C$_6$H$_{12}$COOH(Na) | —H |
| —H | —H | —C$_6$H$_{13}$ | —H | —SO$_3$H(Na) |
| —H | —H | —H | —COOH(Na) | -tert-Butyl |
| —H | —CH$_2$NH$_2$ | —H | —H | —H |
| —H | —H | —H | —H | —NH$_2$ |
| —OH | —H | —H | —H | —CH$_2$NH$_2$ |
| —H | —H | —H | —H | —C$_4$H$_8$NH$_2$ |
| —H | —H | —H | —COOCH$_3$ | —COOH(Na) |
| —OH | —H | —H | —COONHCH$_3$ | —H |
| —H | —H | —H | —COONHCH$_3$ | —COOH(Na) |
| —H | —H | —H | -imidazoyl | —H |
| —H | —H | —H | -glycinyl | —H |
| —H | —H | —H | -steroidyl | —H |
| —H | —H | —H | -glycosyl | —H |
| —H | —H | —H | —H | -imidazoyl |
| —H | —H | —H | —H | -glycinyl |
| —H | —H | —H | —H | -steroidyl |
| —H | —H | —H | —H | -glycosyl |

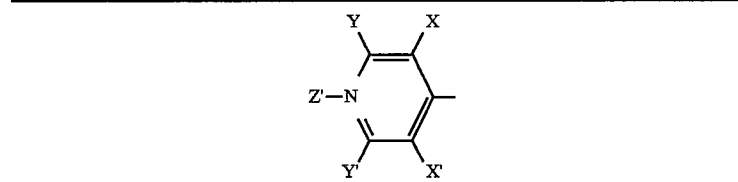

| X | X' | Y | Y' | Z' |
|---|---|---|---|---|
| —H | —H | —H | —H | —H |
| —H | —H | —H | —H | —CH$_3$ |

-continued
| | | | | |
|---|---|---|---|---|
| −H | −H | −H | −H | −C$_6$H$_{12}$OH |
| −H | −H | −H | −OH | −H |
| −H | −H | −OH | −H | −H |
| −H | −H | −H | −COONHCH$_3$ | −H |
| −H | −H | −H | −H | -benzyl |
| −H | −H | −H | −C$_6$H$_{12}$OH | −CH$_3$ |
| −H | −H | −C$_6$H$_{13}$ | −H | −CH$_3$ |
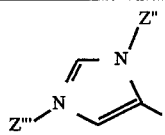
| Z'' | Z''' |
|---|---|
| −H | −H |
| −CH$_3$ | −H |
| −H | −CH$_3$ |
| −H | −C$_6$H$_{12}$ |
| −C$_6$H$_{12}$ | −H |
Specific examples of such compounds include:
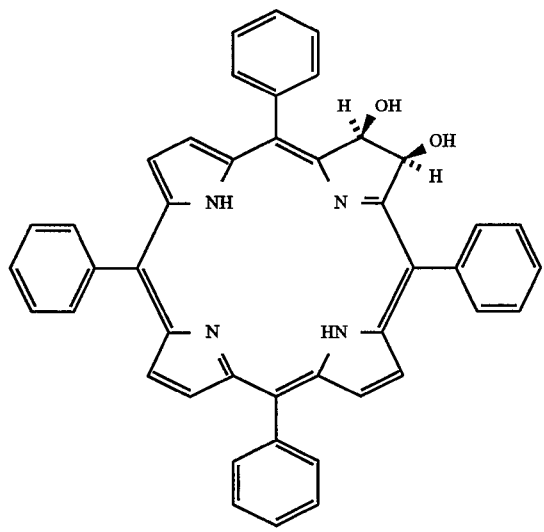
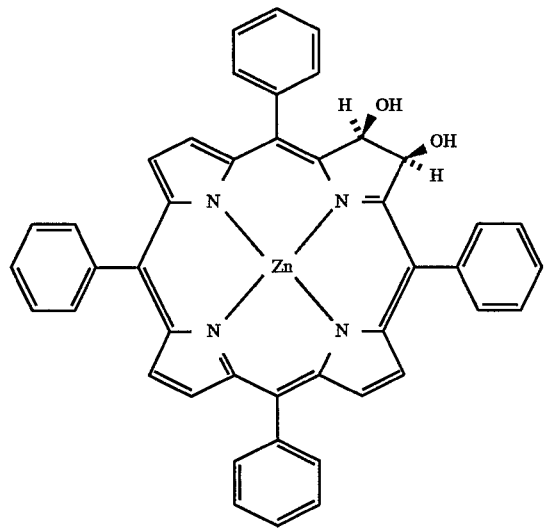

-continued
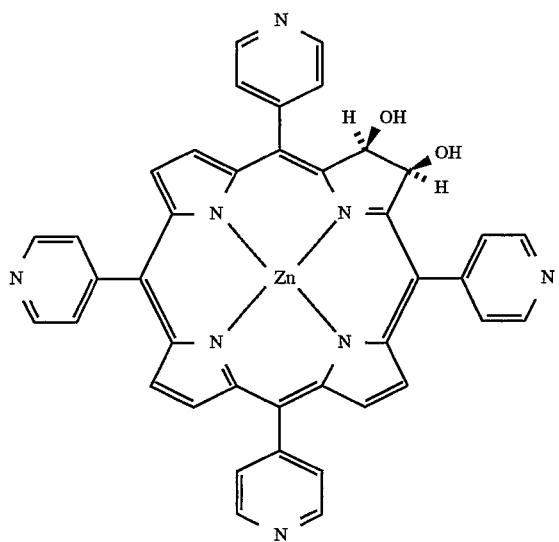
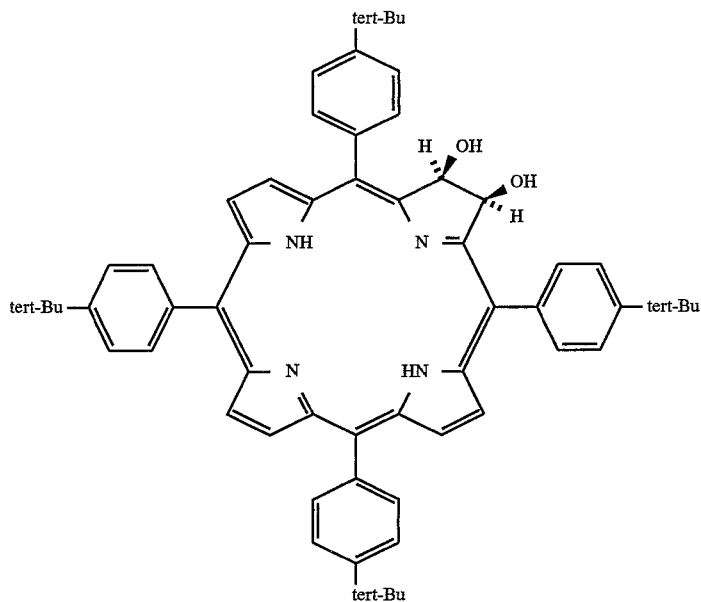

-continued
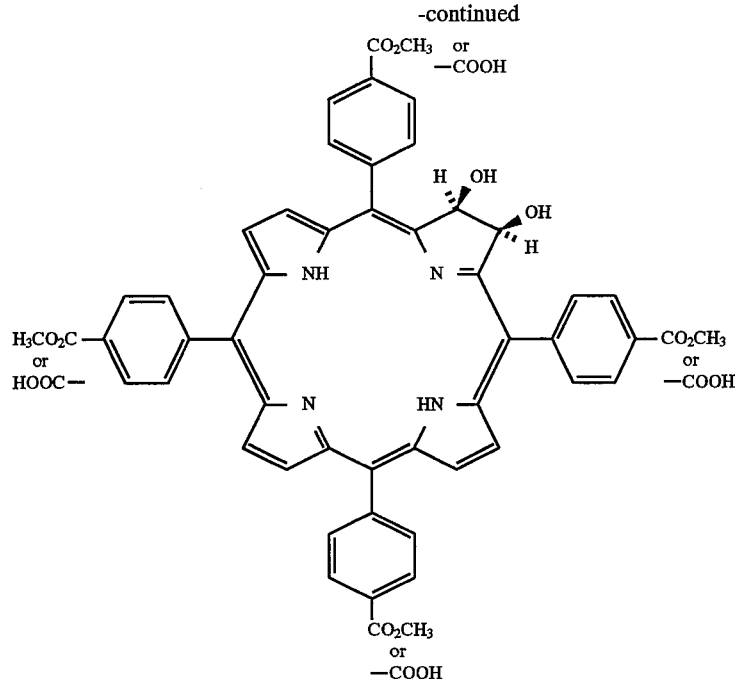
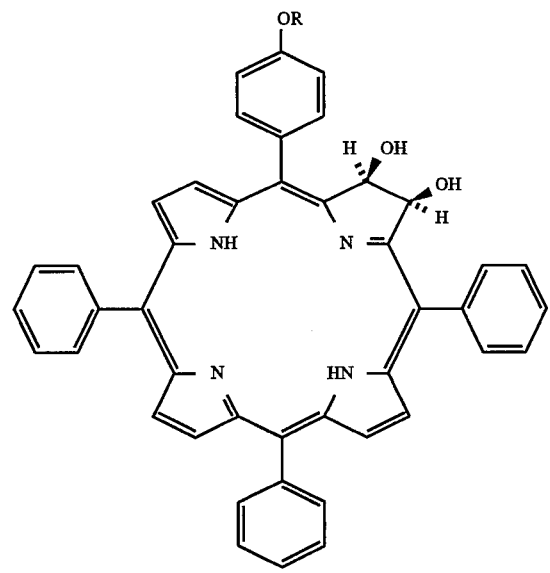

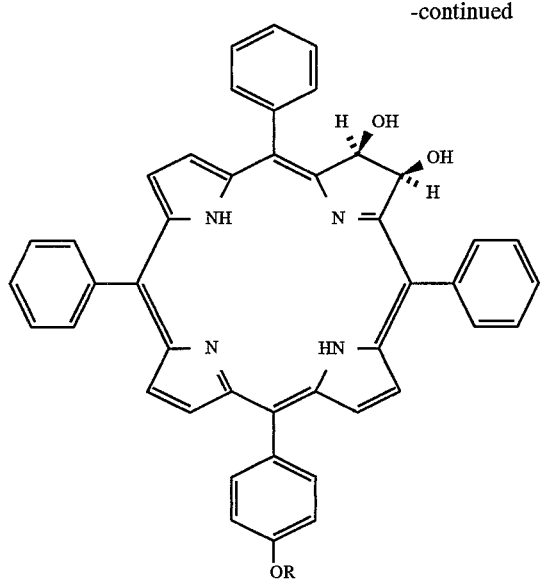
where R = H, C$_6$–C$_{18}$ alkyl or a fatty acid;
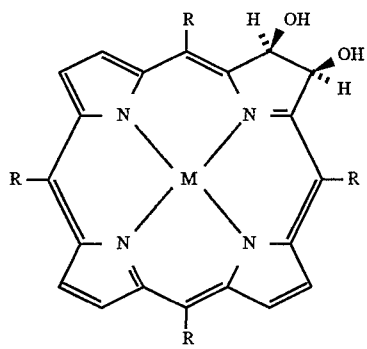
where R is methyl, ethyl or propyl; and
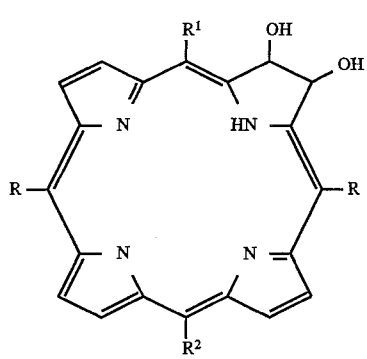
Substituents
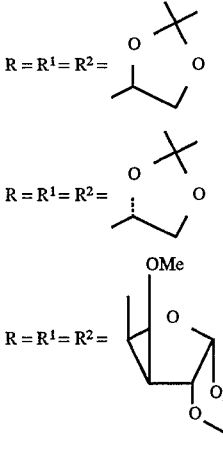
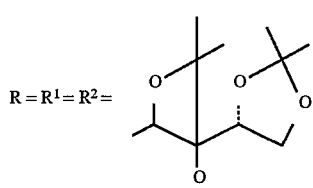

-continued
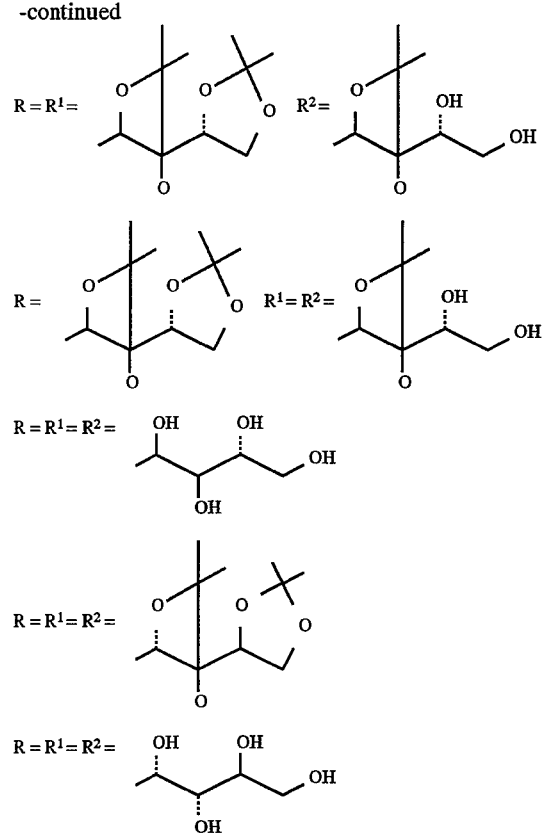
Examples of both cationic and anionic water soluble chlorin compounds include:
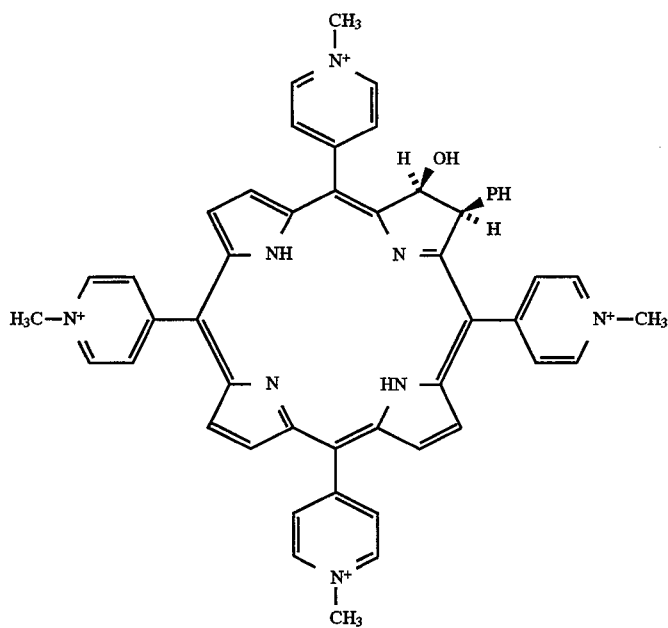
and -continued

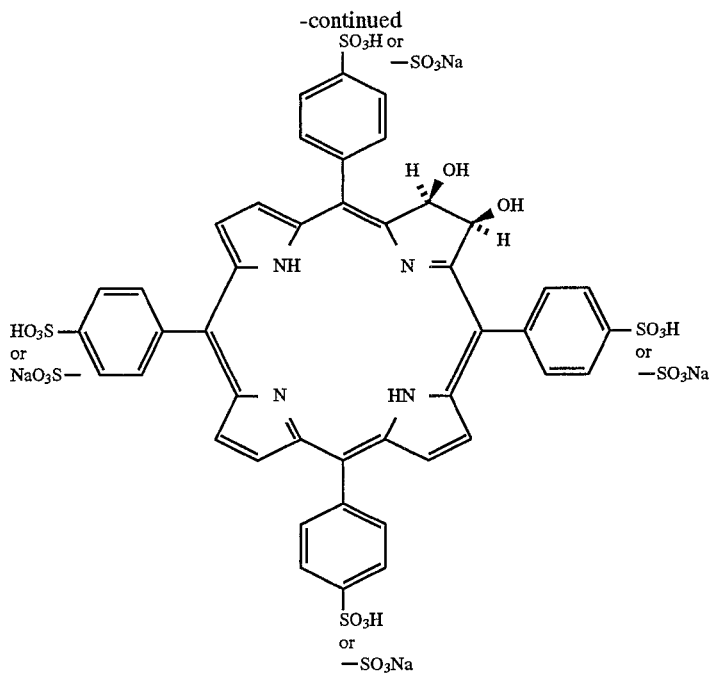

Step "a." of the process of making the compounds of the invention comprises osmylating a meso-substituted metalloporphyrin of formula (III), or the corresponding demetallated porphyrinogenic of formula (IV), to form an osmate ester at the β,β'-position. The starting meso-substituted metalloporphyrin (III) or porphyrin (IV) for this reaction can be prepared by any one of a number of standard procedures. Examples include such techniques as:

(1) Pyrrole and appropriately substituted benzaldehydes can be reacted by the Adler method, in accordance with Adler et al., "A Simplified Synthesis for meso-Tetraphenylporphyrin", *J. Org. Chem.*, 32, 476 (1967), or by the Lindsey method, as described in "Investigation of a Synthesis of meso-Porphyrins Employing High Concentration Conditions and an Electron Transport Chain for Aerobic Oxidation", *J. Org. Chem.*, 59, 579–87 (1994). Similar reactions are described for meso-tetraalkyl compounds in "Facile Syntheses of Tetraalkylchlorin and Tetraalkylporphyrin Complexes and Comparison of the Structures of the Tetramethylchlorin and Tetramethylporphyrin Complexes of Nickel (II), *J. Am. Chem. Soc.*, 102:6852–54 (1980).

(2) The condensation of dipyrrolic compounds and their counterparts, as described by Wallace et al., "Rational Tetraphenylporphyrin Syntheses: Tetraarylporphyrins from the MacDonald Route", *J. Org. Chem.*, 58, 7245–47 (1993).

(3) The manipulation of a porphyrin at its β- or meso-positions, for example, as described by Di Magno et al., "Facile Elaboration of Porphyrins Via metal-Mediated Cross-Coupling", *J. Org. Chem.*, 58, 5983–93 (1993); or by Osuka et al., "Synthesis of 5,15-Diaryl-Substituted Oxochlorins from 5,15-Diaryl-octaethyl Porphyrin, *Bull. Chem. Soc. Japan*, 66, 3837–39 (1993); or the manipulation of phenyl substituents on a preexisting and appropriately substituted mesophenylporphyrins described by Hombrecher et al., "An Efficient Synthesis of Tetraaryl Porphyrins Substituted with Ester Groups Bearing Long Alkyl Chains", *Tetrahedron*, 49:12, 2447–56 (1993).

The disclosures of all of the above documents are hereby incorporated by reference.

Preferably, the compound of formula (III) used as the starting material for step "a." is prepared by using the Lindsey et al. method for synthesizing porphyrins (see above). A general procedure for carrying out such a reaction is set forth below: Typically, an equimolar mixture of pyrrole and an appropriately substituted benzaldehyde are reacted under a nitrogen atmosphere with acid catalysis. Oxidation of the formed porphyrinogen with air or treatment with DDQ as an oxidant gives the porphyrin, which is then typically purified by column chromatography.

The osmylation reaction of step "a." is be carried out by treating the starting material with $OsO_4$ in the presence of a base, typically pyridine, thus forming an osmate ester at the β,β'-position, as shown below:

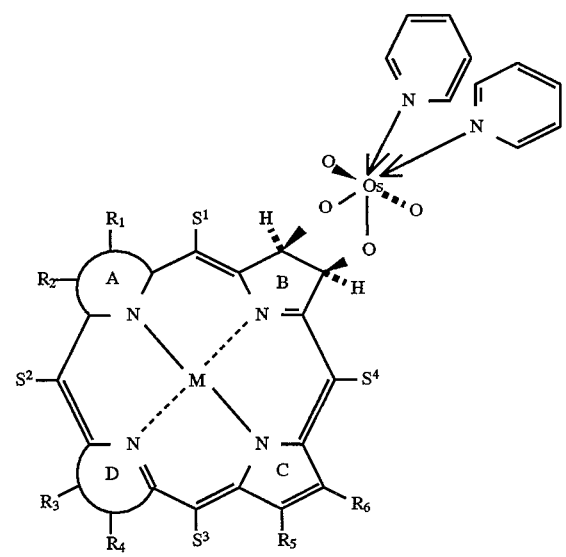

or

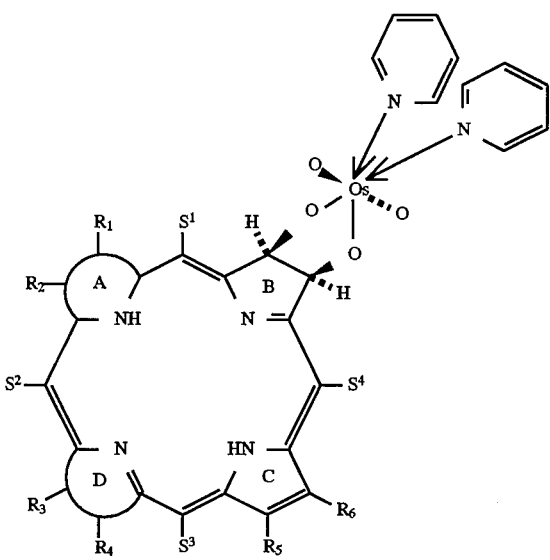

The amount of the OsO$_4$ is generally stoichiometric, and typically varies from about 1.0 to about 1.5 moles OsO$_4$ per mole of starting material.

The base usually used with the OsO$_4$ is generally one that is able to coordinate to the osmium(IV) in the osmate ester and that, thereby, stabilizes this intermediate and speeds up the formation of the osmate ester. See, for example, Schroder, "Osmium Tetroxide Cis Hydroxylation of Unsaturated Substrates", *Chem. Rev.*, 80:187–218 (1980). Preferred bases include pyridine, imidazole, isoquinoline, tert-alkyl amines such as trimethylamine, methylsulfonamide and the like. The amount of base used can vary widely, so long as a sufficient amount is present saturate the coordination sphere of the osmium(VI) in the osmate ester. Preferably, however, the amount of base used falls within the range of about 2 to about 20 equivalents. Some bases, such as pyridine, can also be used as solvents or co-solvents for the osmylation reaction.

While the OsO$_4$ can be added to a reaction mixture neat, it is best used dissolved in a suitably non-reactive solvent. When used, the choice of a solvent depends on the substituent pattern on the porphyrin starting material, which affects its solubility. However typically encountered solvents include aromatic solvents, such as pyridine, toluene and benzene; chlorinated solvents, such as CHCl$_3$ and dichloromethane; water; ethers, such as diethyl ether, tetrahydrofuran, diethylene glycol and glycol dimethyl ether (ethylene glycol dimethyl ether); ketones such as acetone and methyl ethyl ketone; acetonitrile; DME, DMF and DMSO; alcohols such as ethanol, methanol and butanol; and mixtures thereof.

When the starting material is water-soluble, the preferred solvent is water. When an organic solvent is used, particularly useful solvent systems include combinations of chlorinated solvents, such as CHCl$_3$ and dichloromethane, mixed with about 2–25 volume % pyridine.

The temperature of the reaction mixture during step "a." can vary widely but, typically, is maintained at room temperature or cooled somewhat to a temperature in the range of about −10° C. to room temperature. Preferably, the reaction is carried out at about room temperature.

The time required for the osmylation reaction of step "a." will depend to a large extent on the temperature used and the relative reactivities of the starting materials. Particularly when the meso-substituents are aryl or a bulky alkyl group, such as tert-butyl, the reaction time tends to be relatively slow due to steric hindrance of the β-positions against the attack of the incoming osmium (VIII) species of OsO$_4$ (complexed with a base such as pyridine). Thus, even though di-meso-substituted systems have been observed to react relatively quickly, the tetra-substituted systems, at least where one or more of S$^1$ through S$^4$ are particularly bulky such as a tert-butyl group, a cycloalkyl group, or a substituted phenyl ring, may require a significantly longer time to go to completion. Therefore, the reaction time can vary greatly, for example, from about 1 hour to about 7 days.

The osmylation reaction can be carried out at pressures both above and below atmospheric pressure. Preferably, however, the reaction is carried out at a pressure about equal to atmospheric pressure. The reaction can be carried out in the presence of a mixture of gases approximating air but, when particularly reactive reactants are involved, the gaseous mixture may be enriched with an inert gas, such as nitrogen gas, argon, and the like.

The osmylation step of the invention can be carried out under conditions of normal, ambient lighting. However, because the substrates and products of the osmylation are often good photosensitizers, the exclusion of light is generally preferred to minimize side reactions.

The progress of the reaction sometimes involves a color change of the reaction mixture, for example, from purple to green. If desired, this color change can be used to monitor the approximate degree of completion of the reaction. Other known techniques, such as various types of chromatography, especially TLC and HPLC, can also be used to follow the progress of the reaction by the disappearance of the starting material.

At the conclusion of the osmylation reaction, a reaction mixture results, from which the diol product is separated and purified by any conventional means, typically chromatographically. Preferably, however, the osmylation reaction mixture is used directly in the reduction step "b." without the intervening isolation or purification of the intermediate(s) present in the reaction mixture being necessary.

The reduction of the osmylation reaction mixture to form the diol of formula (I) can be accomplished by many of the usual reducing agents. Examples of such useful reducing agents include gaseous H$_2$S, HSO$_3^-$, BH$_4^-$, AlH$_4^-$, B$_2$H$_6$, H$_2$ with a Ni- or Pd- catalyst, Zn/H+ and the like. However, particularly convenient reductants include H$_2$S and HSO$_3^-$, of which H$_2$S is more preferred.

Most of the above reducing agents are used in combination with a suitably non-reactive organic or inorganic non-solvent, such as methanol, ethanol and the like, to aid in solubilizing the polar dihydroxylated product, especially when the product is an anionic or cationic species. A co-solvent sometimes also facilitates the isolation and purification of the product. A particularly preferred combination of reducing agent and non-solvent for step "b." is H$_2$S with methanol.

Specific examples of reducing agents that are particularly useful for direct addition to the reaction mixture at the end of the osmylation step "a.", without the intervening isolation or purification of specific compounds in the osmylation reaction mixture, include: (1) treatment with H$_2$S and methanol; and (2) vigorous stirring of the organic phase with a solution of HSO$_3^-$ in H$_2$O. In such cases, reduction may proceed at a satisfactory rate, as commonly occurs with the first method, or the reaction may occur dependably but at rate that may be significantly slower, as sometimes occurs with the second method. Thus, the rate of the reaction is often influenced by the type and combination of reducing agent, with or without the presence of a non-solvent to precipitate out the unused reducing agent.

The temperature of the reaction mixture during the reduction step "b." can vary widely depending upon the reducing agent being used. For example, when gaseous $H_2S$ is being used as the reducing agent, the temperature is typically allowed to remain at about room temperature. When other reducing agents, however, the temperature can range from about 1° to about 100° C.

The time required for the reduction reaction of step "b." will depend to a large extent on the temperature used and the relative reactivities of the starting materials but, preferably, is about room temperature. The reduction reaction of step "b." can be carried out in the presence of gases at a pressure both above and below atmospheric pressure. Most frequently, however, the reaction is carried out at a pressure about equal to atmospheric pressure.

The resulting product, a $\beta,\beta'$-dihydroxy meso-substituted chlorin, bacteriochlorin or isobacteriochlorin compound of formula (I) or formula (II), can be isolated by any conventional method, such as by drowning out in a non-solvent, precipitating out, extraction with any immiscible liquid, evaporation of a solvent, or some combination of these or other conventional methods. Typically, the $\beta,\beta'$-dihydroxy compound of formula (I) or formula (II) may then be purified by any one or a combination of known purification techniques, such as recrystallization, various forms of column chromatography, trituration with a non-solvent or a partial solvent, countercurrent extraction techniques, and the like.

A general procedure for accomplishing a typical osmylation-reduction is set forth below:

A known amount of 5,10,15,20-meso-tetraphenylporphyrin is suspended in a solvent mixture of about 40:1 $CHCl_3$:pyridine and mixed with 1.3 equivalents $OsO_4$. The reaction mixture is stirred in the dark for about 4 days. The reaction is quenched by purging with gaseous $H_2S$ for a few minutes. After adding methanol, the precipitated black OsS is filtered off. The filtrate is evaporated to dryness, chromatographed, for example, on silica/$CH_2Cl_2$-0.5% methanol, and further purified by recrystallization.

Where the demetallated $\beta,\beta'$-dihydroxy compound of formula (II) is desired, demetallation can take place at one of several stages during the process of the invention. One can either (1) start with the demetallated meso-substituted porphyrinogenic compound having the formula (IV) shown below:

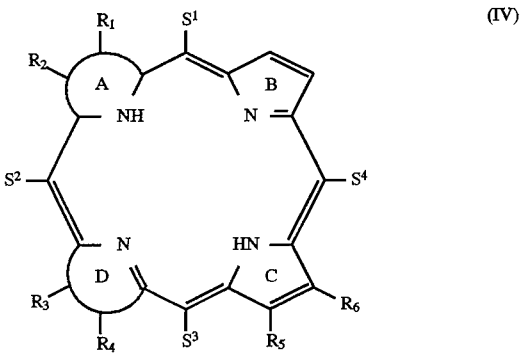

or (2) osmylate the meso-substituted metalloporphyrin and remove the metal M from the compounds making up the reaction mixture after the osmylating step "a" and prior to the reducing step "b"; or (3) demetallate the $\beta,\beta'$-dihydroxy meso-substituted compound of formula (I) after the reducing step "b" to form a compound of formula (II).

The presence of the metal M is not generally required to carry out either the osmylation step "a" or the reduction step "b". However, in many cases, having a metal ion present increases the solubility of the starting material of the reaction, thus enabling a higher concentration of reactants and a shorter reaction time. Therefore, it is believed to be advantageous to have the metal present, particularly during the osmylation step "a" of the process of the invention. However, it should be noted that, in addition to the metal, other substituents on the meso-substituted compound may also have a significant effect on the solubility of the compound and thus also influence the concentration and reaction time.

Whether the $\beta,\beta'$-dihydroxy compound of formula (I), or the corresponding compounds after the osmylating step "a", or the corresponding compounds after the reduction step "b", are being demetallated, the reaction conditions are usually the same or very similar. Suitable demetallating reagents used for this purpose include any acid that is capable of demetallating, but which does not induce the formation of oxo-porphyrins. Also the demetallating conditions should be selected to be compatible with the particular substituents present on the compound being demetallated.

Typically, concentrated mineral acids, such as sulfuric acid and hydrochloric acid should be avoided because they are often sufficiently harsh to rearrange/dehydrate the diol substrate to form the corresponding oxo-porphyrin, as well as demetallating the compound. Preferably, the demetallating agent is selected from the group consisting of $CH_3COOH$, $CF_3COOH$, $H_2S$, 1,3-propanedithiol, dilute hydrochloric acid in a suitable solvent such as water or chloroform, and mixtures thereof. Examples of suitable mixtures of demetallating agents include: (1) dilute trifluoroacetic, (2) $H_2S$, and (3) a two-phase system formed by chloroform and dilute (5%) aqueous hydrochloric acid.

Although demetallation reactions are known to those of ordinary skill in this art, additional information can be obtained in J. W. Buchler, "Synthesis and Properties of Metalloporphyrins", The Porphyrins, Vol. I, Chapter 10 (2978). The above demetallating agents can sometimes be used in combination with a suitably non-reactive solvent. Examples of useful solvents include water; alcohols, such as ethanol, methanol, iso-propanol and the like; haloalkanes such as methylene chloride and the like; nitrogen-containing solvents such as DMF, tetrahydrofuran and the like; relatively unreactive aromatic compounds such as benzene, toluene and the like; and ethers such as diethyl ether, diethylene glycol, and glycol dimethyl ether.

The temperature of the reaction mixture during the demetallating process can vary widely but, typically, is maintained in the range of about 0° to 120° C. For example, refluxing acetic acid can be used as a demetallating agent in some circumstances, which would provide a temperature of about 118° C. However, the demetallating reaction is most preferably carried out at about room temperature or below.

The time required for demetallation varies widely, depending on the temperature used and the relative reactivities of the starting materials, particularly the demetallating agents and the metal to be removed from the porphyrin. For example, when a two-phase system of 5% aqueous hydrochloric acid and chloroform is used to demetallate a zinc porphyrin, the reaction typically takes place in minutes. If, on the other hand, rearrangement is desirable, the metallated compound can be subjected to stronger acid conditions, such as dry hydrochloric gas in chloroform, to accomplish the rearrangement, remove the metal, or both.

The reaction can be carried out above or below atmospheric pressure. Preferably, the reaction is carried out at a pressure about equal to atmospheric pressure. Straightforward procedures can be used to isolate the demetallated product, such as neutralization of the reaction mixture, extraction with any immiscible liquid, eluting on a silica gel column or other types of chromatography, drowning out in a non-solvent, precipitating out or otherwise crystallizing, evaporation of solvent, or some combination of these or other conventional methods. Preferred methods of isolating the desired demetallated compound include chromatography and/or crystallization. If further purification of the demetallated product is desired, it may be subjected to additional purification procedures, such as recrystallization, eluting on a silica gel chromatography column, and combinations of these methods.

Because of the mechanism of the $OsO_4$ oxidation of olefins, the $\beta,\beta'$-dihydroxy compounds resulting from step "a." and step "b." are vicinal diols. The introduction of the $[CH_2Cl_2$-0.5% MeOH$]$=708 nm, log $\epsilon$=4.89). This increase in the log $\epsilon$ values of $\lambda_{max}$ means that the chlorin absorbs light about 4.0 times more efficiently in the red region of the spectrum than the parent porphyrin, as a result of intensified Q bands.

Further still, the compounds of the invention are surprisingly stable toward dehydration and concomitant reconstitution of the porphyrin chromophore. For example, it has now been found that dilute HCl in $CHCl_3$ under reflux conditions can be successfully used to demetallate a chlorin of formula (I) where M is Zn, but without provoking undesirable rearrangement reactions. To purposely accomplish the expected dehydration and rearrangement to the corresponding oxo compound, as shown below, a catalytic amount $HClO_4$ must also be added.

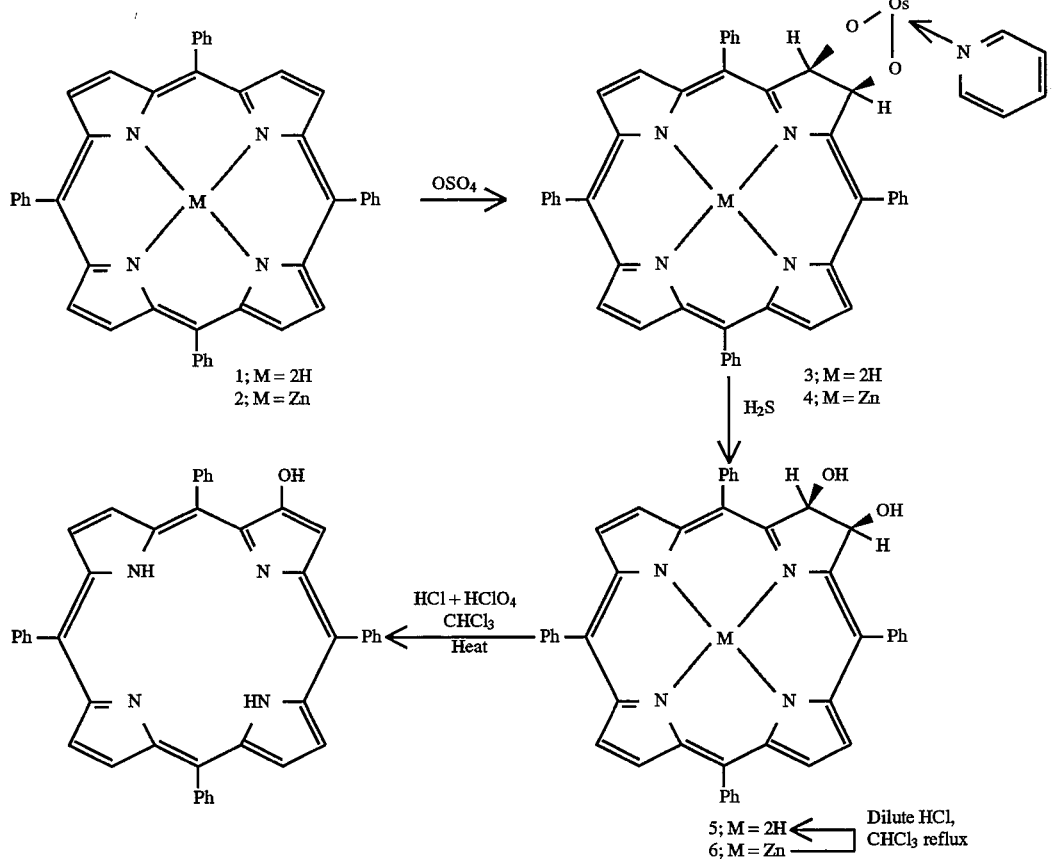

vic-diol gives the molecule an amphiphilic character, a property believed to be important in the biodistribution of site-specific photochemotherapeutics. Moreover, the conversion of a porphyrin into a chlorin changes the optical properties in a desirable direction (tetraphenyl porphyrin, $\lambda_{max}$[benzene]=653 nm, log $\epsilon$=3.80; 2,3-vic-dihydroxy-tetraphenylchlorin, $\lambda_{max}$[$CH_2Cl_2$-0.1% MeOH]=644 nm, log $\epsilon$=4.38). Converting the dihydroxy chlorin into the tetrahydroxy bacteriochlorin, this effect is even more pronounced (2,3,12,13-tetrahydroxy bacteriochlorin, $\lambda_{max}$ Likewise, when meso-tetraphenylchlorin is treated with a stoichiometric amount of $OsO_4$, followed by reduction of the intermediate, the 2,3-vic-dihydroxy-meso-tetraphenylbacteriochlorin is produced. However, insertion of Zn(II) as a metal ion into the chlorin changes the outcome to yield, instead, the (2,3-vic-dihydroxyisobacteriochlorinato) $Zn^{II}$, which can be demetallated under mild acidic conditions to produce 2,3-vic-dihydroxyisobacteriochlorin. This sequence of reactions is shown schematically below to illustrate again the directing effect of the central metal when present.

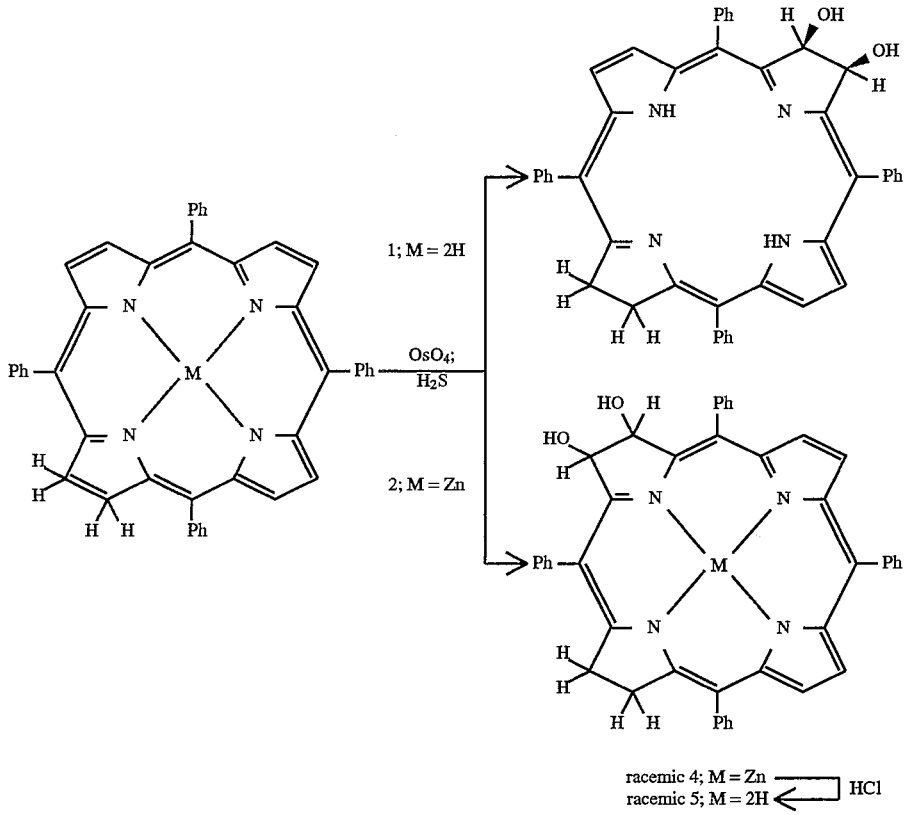

The reason for this phenomenon is not well-understood. Some have suggested that the reduced double bond in a chlorin compound induces a pathway for the delocalized π-electrons that "isolates" the diametrically opposed pyrrolic double bond. Attack is thought to be favored here over the attack of the double bond in the adjacent pyrrolic unit, as it causes a minimal loss of π-energy, leading to the selective formation of a bacteriochlorin compound. The introduction of a metal (or the protonation of the chlorin), it is thought, would cause a change of the preferred π-localizing pattern, "isolating" the double bond on an adjacent pyrrolic unit and resulting in the formation of a metallo-isobacteriochlorin.

The β,β'-dihydroxy meso-substituted chlorin, bacteriochlorin and isobacteriochlorin compounds of the invention can also be subjected to reaction steps "a" and "b" a second time to add a second pair of hydroxy groups. The relative position of the second pair of hydroxy groups depends on many factors, such as the presence of a metal, the selection of the metal when one is present, the relative bulk and electronic characteristics of the meso-substituents, and the presence and characteristics of additional β,β'-substituents.

Of particular interest, again, is the role of the metal M in directing a second pair of hydroxy substituents to preferred positions. For example, when a demetallated diol chlorin of formula (II) is osmylated and reduced in accordance with the process of the invention, the second pair of hydroxy groups goes to the β,β'-positions on the opposite ring. Conversely, if a metallated compound of formula (I) is used, e.g., one where M is zinc, the second pair of hydroxy groups is added to the β,β'-positions of an adjacent ring. This phenomenon has also been observed with respect to other reactions, for example, in the diimide reduction of porphyrins described in Whitlock et al., "Diimide Reduction of Porphyrins", *J. Am. Chem. Soc.*, 91, 7485–89 (1969); in the OsO$_4$ oxidation of octaalkyl chlorins described in Chang et al., *J. Chem. Soc., Chem. Comm.*, 1213–15 (1986); in the Raney nickel-catalyzed reduction of Ni$^{II}$ pheophorbides as described in Smith et al., *J. Am. Chem. Soc.*, 107, 4954–55 (1985); and in the OsO$_4$ oxidation of pheophorbides described in Pandey et al., *Tetrahedron Lett.*, 33, 7815–18 (1992).

When a diol chlorin is β,β'-dihydroxylated, a 1:1 mixture of two isomers of 2,3,12,13-bis-(vic-dihydroxy) bacteriochlorins are formed, as shown below.

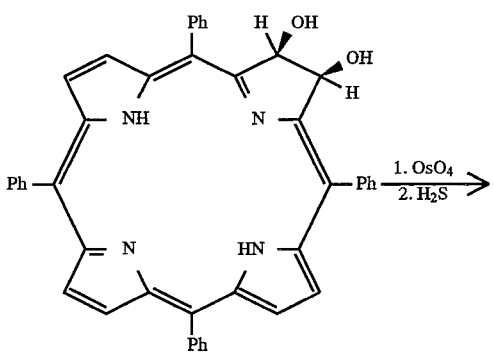

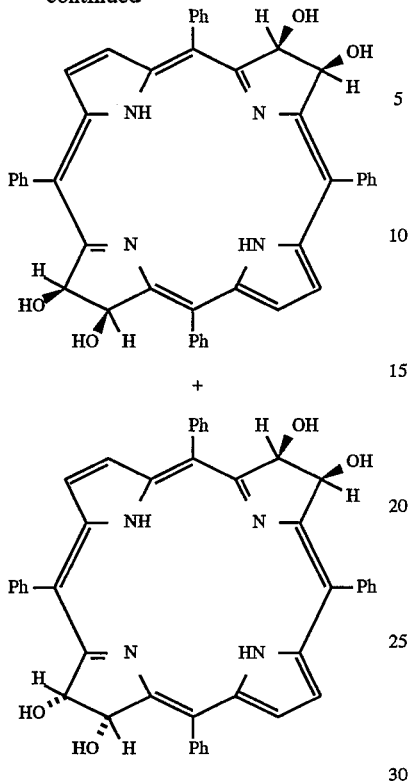

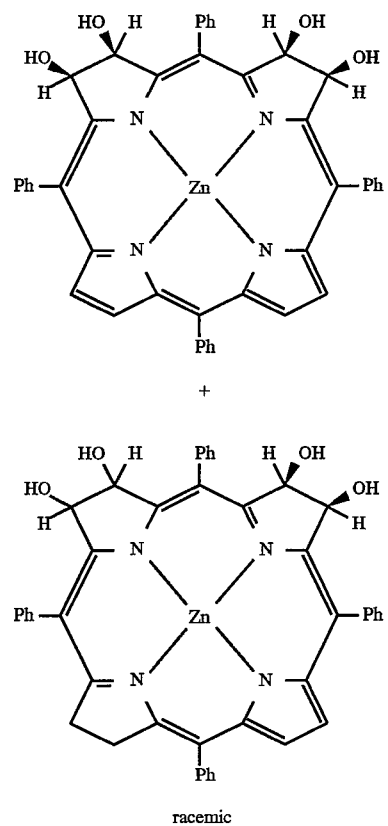

racemic

The isomer carrying the hydroxyl groups on one side of the plane of the porphyrin is, due to its higher polarity, separable from its isomer by column chromatography. This isomer has a pronounced amphiphilic character from bearing all polar functionalities on one side of the molecule. The absorption characteristics of the hydroxy bacteriochlorins are in a "preferred" range for use as photosensitizers in photodynamic therapy.

When the corresponding zinc-metallated diol chlorin is further β,β'-dihydroxylated, the result is a 1:3 mixture of tetraol metalloisobacteriochlorins (the lower structure being more prevalent), as shown below:

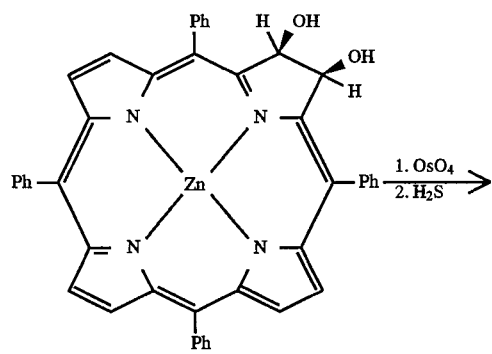

While not completely understood at this time, steric reasons are believed to cause this deviation from a 1:1 mixture. The lower compound ($C_2$ point group) occurs as a racemic mixture, while the upper compound ($C_S$ point group) is not chiral.

The β,β'-dihydroxy meso-substituted chlorin, bacteriochlorin or isobacteriochlorin compounds of the invention can also be dehydrated under acid catalysis to form the corresponding 2-oxy-(meso-tetraphenyl)porphyrins, if desired, thus forming the beginning of yet another synthetic pathway to this known class of compounds. While a few of these compounds are accessible via other methods, e.g. Catalano et al., "Efficient Synthesis of 2-Oxy-5,10,15,20-tetraphenylporphyrins from a Nitroporphyrin by a Novel Multistep Cine-substitution Sequence", *J. Chem. Soc., Chem. Comm.*, 1537–38 (1984), many other compounds can be prepared via the dihydroxylation method of the invention. Specific examples of such compounds are shown below and include:

(A) 2-oxy-12,13-dihydro-meso-tetraphenyl porphyrin;
(B) 2-oxy-7,8-dihydro-meso-tetraphenyl porphyrin; and
(C) 2,12-dioxo-meso-tetraphenyl porphyrin.

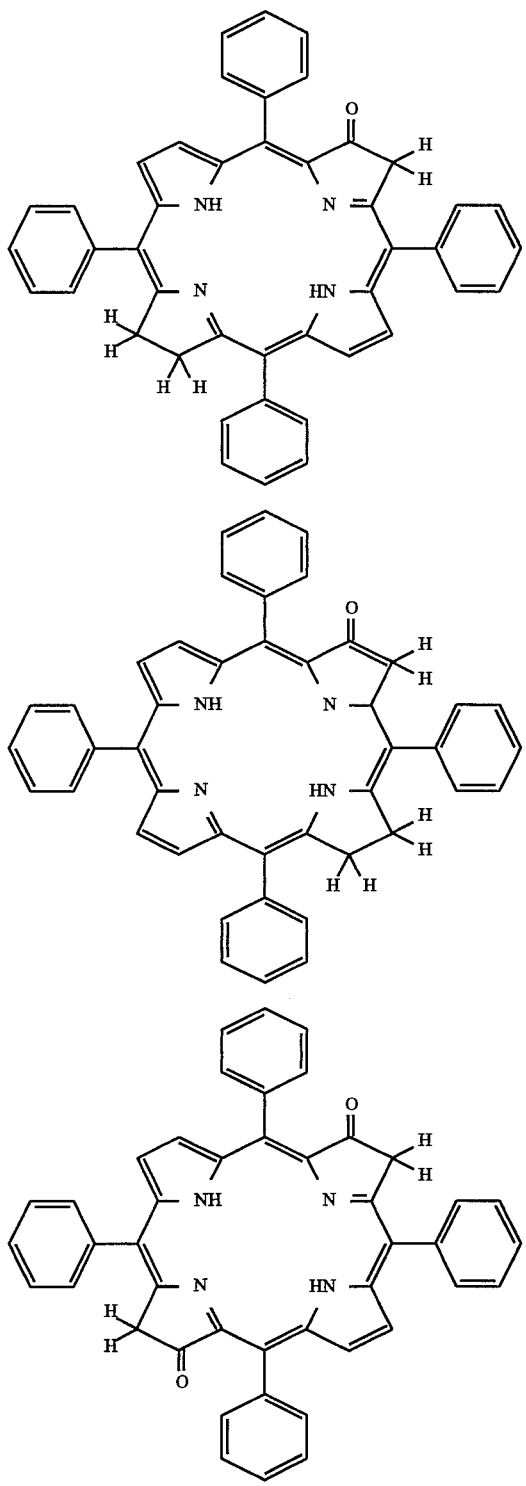

Other synthetic pathways of potential interest include the formation of a isopropylidene ketal, which may confer the ability to fine tune solubilities, biodistribution properties and amphiphilicities of the compounds of the invention even further, and without losing valuable spectral qualities.

The β,β'-dihydroxy meso-substituted chlorin, bacteriochlorin and isobacteriochlorin compounds of the invention are useful as photosensitizers used in photodynamic therapy (PDT) and as synthetic intermediates for making related photosensitizers. Specifically, these photosensitizers are useful in sensitizing neoplastic cells or other abnormal tissues to destruction by irradiation with visible light. Upon photoactivation, the energy of photoactivation is believed to be transferred to endogenous oxygen, thus converting it to singlet oxygen. This singlet oxygen is thought by some to be responsible for the observed cytotoxic effect. Alternatively, there may be direct electron transfer from the photoactivated molecule. The method of van Lier, *Photobiological Techniques*, 216, 85–98 (Valenzo et al. eds. 1991) can be used to confirm the ability of any given compound to generate singlet oxygen effectively, thus making it a good candidate for use in photodynamic therapy. In addition, the photoactivated forms of porphyrin are able to fluoresce, and this fluorescence can aid in imaging a tumor.

Typical indications known in the art include diagnosis and destruction of tumor tissue in solid tumors, such as those of bronchial, cervical, esophageal or colon cancer; dissolution of plaques in blood vessels (see, e.g., U.S. Pat. No. 4,512, 762, which is hereby incorporated by reference); treatment of topical conditions such as acne, athlete's foot, warts, papilloma and psoriasis; and treatment of biological products, such as blood for transfusion to eliminate infectious agents.

Additionally, when metals such as In or Tc are used, the metallated pigment compounds of the invention have diagnostic use in nuclear medicine. Similarly, when M is Mn(III) or Gd(III), the compounds may be useful in magnetic resonance imaging. These are also applications where, due the variability possible with respect to the substitution patterns, significantly improved biodistribution properties may be achieved by using the compounds of the invention.

The photosensitizers made from the compounds of the invention can be formulated into pharmaceutical compositions for administration to the subject or applied to an in vitro target using techniques generally known in the art. A summary of such pharmaceutical compositions may be found, for example, in Remington's Pharmaceutical Sciences, Mack Publishing Co., Easton, Pa. The compounds of the invention can be used singly or as components of mixtures.

Generally, for the diagnosis or treatment of solid tumors, the compound of the invention, labeled or unlabeled, is administered systemically, such as by injection. Injection may be intravenous, subcutaneous, intramuscular, or even intraperitoneal. Injectables can be prepared in conventional forms, either as liquid solutions or suspensions, solid forms suitable for solution or suspension in a liquid prior to injection, or as emulsions. Suitable excipients are, for example, water, saline, dextrose, glycerol and the like. Of course, these compositions may also contain minor amounts of nontoxic, auxiliary substances, such as wetting or emulsifying agents, pH buffering agents, and so forth.

Systemic administration can be implemented through implantation of a slow release or sustained release system, by suppository, or, if properly formulated, orally. Formulations for these modes of administration are well known in the art, and a summary of such methods may be found, for example, in Remington's Pharmaceutical Sciences (supra).

If treatment is to be localized, such as for the treatment of superficial tumors or skin disorders, the compound can be administered topically using standard topical compositions, such as lotions, suspensions, or pastes.

The quantity of the photosensitizer compound to be administered depends upon the choice of active ingredient, the condition to be treated, the mode of administration, the individual subject, and the judgment of the practitioner. Depending on the specificity of the preparation, smaller or larger doses may be needed. For compositions that are highly specific to target tissues, such as those with a highly specific monoclonal immunoglobulin preparation or a specific receptor ligand, dosages in the range of 0.05–1 mg/kg are suggested. For compositions that are less specific to the target tissue, larger doses, up to 1–10 mg/kg may be needed. The foregoing ranges are merely suggestive, as the number of variables in regard to an individual treatment regime is large, and considerable excursions from these recommended values are not uncommon.

In addition to in vivo use, the compounds made from the intermediate compounds of the invention can be used in the treatment of materials in vitro to destroy harmful viruses or other infectious agents. For example, blood plasma or blood that is to be used for transfusion or banked for future transfusion, can be treated with the compounds of the invention and irradiated to effect sterilization. In addition, biological products such as Factor VIII, which are prepared from biological fluids, can be irradiated in the presence of the compounds of the invention to destroy contaminants.

Further, because the $S^1$ through $S^4$ groups in the four meso positions can be the same or different, or substituted either symmetrically or asymmetrically, the compounds of the invention can be "fine tuned" to produce a desired set of biological effects when administered to a subject in need of photodynamic therapy. As a specific example, to "fine tune" the solubility, biodistribution, and/or amphiphilicities of the compounds of the invention, the corresponding isopropylidene ketal may be formed. Further still, the invention provides methods for synthesizing such derivative compounds in an efficient manner with relatively few by-products or isomeric impurities.

The invention will be further clarified by the following examples, which are intended to be purely illustrative of the invention.

Example 1: β,β'-Dihydroxylation of Tetraphenylporphyrin to Make 3,4-Dihydroxy-5,10,15,20-tetraphenylchlorin four days. The reaction was quenched by purging with gaseous $H_2S$ for five minutes. Following the addition of 20 ml of methanol, the precipitated black OsS was filtered off through diatomaceous earth (commercially available under the trade name Celite). The filtrate was evaporated to dryness, and the residue was charged onto a silica gel column (200 g, 280–400 mesh) and eluted with 1,1-dichloromethane to remove the unreacted starting material (400 mg, 40%). A mixture of 1.5% methanol in 1,1-dichloromethane was used to elute the desired β,β'-dihydroxychlorin product (520 mg, $8.02 \times 10^{-4}$ mol, 49% yield). Finally, 5.0% methanol in dichloromethane eluted a crude mixture of tetrahydroxybacteriochlorins (40 mg, 3.5 %). The desired β,β'-dihydroxychlorin was recrystallized in $CHCl_3$/methanol, m.p. >350° C. The UV-vis spectrum of this β,β'-dihydroxychlorin was typical for chlorins and is shown in FIG. 1.

$R_f$=0.68 (silica gel, $CH_2Cl_2$/1.5% methanol);

$^1$H NMR (400 MHz, $CDCl_3$) δ=−1.78 (br s, 2H, NH); 3.14 (s, 2H, OH, exchangeable with $D_2O$); 6.36 (s, 2H, pyrroline-H); 7.68–7.80 (m, 12H, phenyl-(m,p) -H); 7.92 (d, J=8.5Hz, 2H, phenyl-H); 8.09 (br s, 4H, o-phenyl-H); 8.15 (d, J=8.5Hz, 2H, o-phenyl-H); 8.33 (d, J=7.9Hz, 2H, β'-H); 8.48 (s, 2H, β-H); 8.63 (d, J=7.9Hz, 2H, β''-H);

$^{13}$H NMR (125 MHz, $CDCl_3$)δ=73.9, 113.2, 123.1, 124.2, 126.7, 127.5, 127.7, 127.9, 128.1, 132.2, 132.7, 133.9, 134.1, 135.5, 140.6, 141.2, 141.8, 153.2, 161.4;

UV-Vis ($CH_2Cl_2$-0.1% MeOH): λ[nm] (log ε) 408 (5.27), 518 (4.19), 544 (4.19), 592 (3.85), 644 (4.38);

Fluorescence at 649 nm (excitation wavelength at 408 nm, $1.10 \times 10^{-6}$ M in $CH_2Cl_2$);

LR-MS (EI, 300° C.)m/e (%): 648 (0.5,$M^+$); 646 (0.9,$M^+$-2H); 630 (100,$M^+$-$H_2O$), 614 (42.7);

HR-MS (EI, 250° C.): calc'd for $C_{44}H_{32}N_4O_2$: 648.2525; found 648.2525;

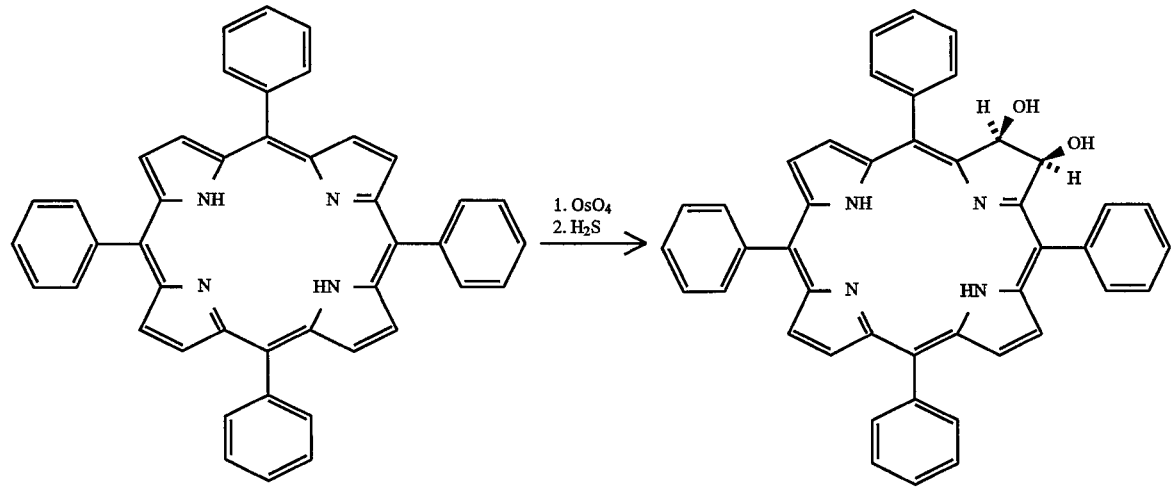

1.00 g ($1.63 \times 10^{-3}$ mol) of 5,10,15,20-meso-tetraphenylporphyrin was suspended in 200 ml of freshly distilled, ethanol-stabilized $CHCl_3$. The resulting mixture was treated with 5.0 ml freshly distilled pyridine and 540 mg ($2.12 \times 10^{-3}$ mol, 1.3 equivalents) $OsO_4$. The reaction flask was stoppered and stirred at room temperature in the dark for Analysis calculated for $C_{44}H_{32}N_4O_2 \cdot \frac{1}{2} H_2O$: C, 80.34; H, 5.06; and N, 8.52; found: C, 80.26; H, 4.93; and N, 8.46.

Example 2: β,β'-Dihydroxylation of Tetraphenylporphyrin to Make 3,4-Dihydroxy-5,10,15,20-tetraphenylchlorinatozinc(II)

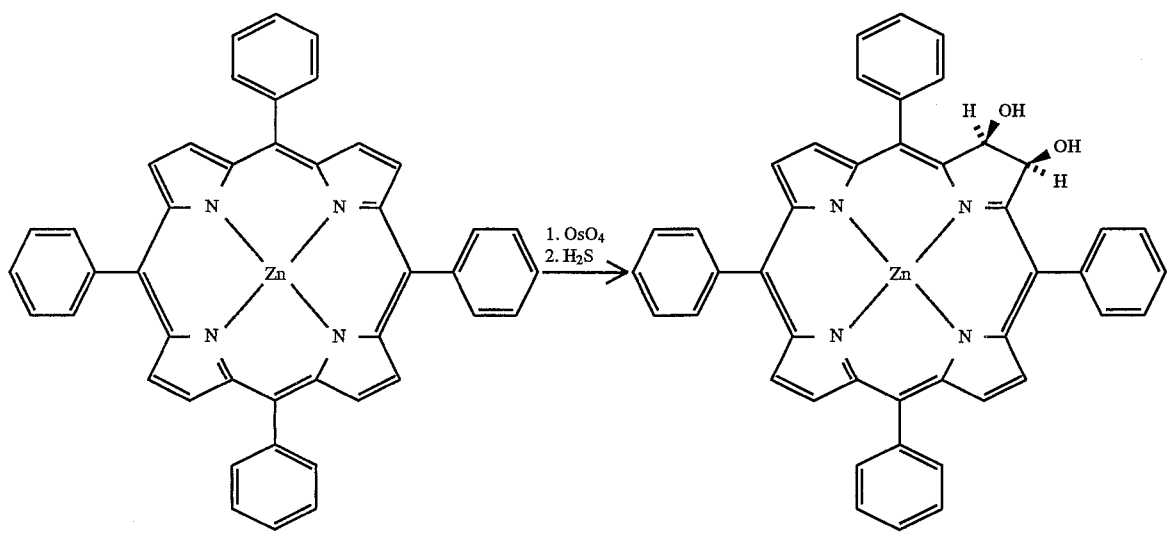

The preparation of the zinc metallated compound analogous to the compound of Example 1 above is based on the procedure of Example 1, except for being adapted to the higher solubility of the metallated starting compound, 5,10,15,20-meso-tetraphenylporphyrinato-zinc(I). 520 mg (7.37× $10^{-4}$ mol) of the starting compound was dissolved in 20 ml of freshly distilled, ethanol-stabilized $CHCl_3$, and treated with 5.0 ml freshly distilled pyridine and 225 mg (8.84×$10^{-4}$ mol, 1.2 equivalents) $OsO_4$. The reaction flask was stoppered and stirred at ambient temperature in the dark for 14 hours. The reaction was quenched by purging with gaseous $H_2S$ for five minutes. Following the addition of 3 ml methanol, the precipitated black OsS was filtered off through a pad of diatomaceous earth (commercially available under the trade name Celite). The filtrate was evaporated to dryness, and the resulting residue was charged onto a silica gel column (100 g, 280–400 mesh) and initially eluted with dichloromethane to remove the unreacted starting material (55 mg, 11I). A mixture of 0.5% methanol in dichloromethane was used to elute the desired β,β'-dihydroxy metallochlorin product (380 mg, 5.34×$10^{-4}$ mol, 72% yield). The desired β,β'-dihydroxy metallochlorin was recrystallized in $CHCl_3$/methanol, m.p. >350° C. The UV-vis spectrum of the β,β'-dihydroxy metallochlorin was typical for metallochlorins and is shown in FIG. 1.

$R_F$=0.62 (silica gel, 1.51 methanol in $CH_2Cl_2$;

$^1$H NMR (300 MHz, $CDCl_3$) δ=5.30 (s, 2H, OH, exchangeable with $D_2O$); 6.12 (s, 2H, pyrrolidine-H); 7.55–7.72 (m, 12H, phenyl-H); 7.81 (dd, J=1.4, 7.5Hz, 2H, phenyl-H); 7.97–8.06 (m, 4H, phenyl-H); 8.08 (d, J=4.5Hz, 2H, β-H), 8.10–8.15 (br m, 2H, phenyl-H); 8.37 (s, 2H, β-H); 8.48 (d, J=4.5Hz, 2H, $^{13}$H NMR (75 MHz, $CDCl_3$): δ=50.633,126.482, 126.585, 126.629, 127.226, 127.351, 127.479, 127.684, 127.766, 127.815, 129.307, 132.114, 132.523, 133.628, 133.680, 133.789, 141.729, 142.573, 146.516, 148.038, 154.217, 156.279;

UV-Vis ($CH_2Cl_2$-0.1% MeOH): λ[nm] (log ε) 418 (5.41), 614 (4.71);

Fluorescence at 620 nm (excitation wavelength at 418 nm, 1.18×$10^{-6}$M in $CH_2Cl_2$);

LR-MS (+FAB, 3-NBA)m/e (%): 710 (29.2,$M^+$); 693 (7.0,$M^+$-OH); 676 (3.7,$M^+$-2OH);

HR-MS (+FAB, 3-NBA): calc'd for $C_{44}H_{30}N_4O_2Zn$: 710.16602; found 710.16595;

Analysis calculated for $C_{44}H_{30}N_4O_2Zn \cdot \tfrac{1}{2}H_2O \cdot \tfrac{1}{2}C_5H_5N$: C, 73.42; H, 4.44; and N, 8.29; found: C, 73.50; H, 4.25; and N, 7.87.

Example 3: The Synthesis of a Water Soluble Chlorin, 2,3-Dihydroxy-5,10,15,20-tetra-(4-pyridyl)-chlorinato zinc (II)

45
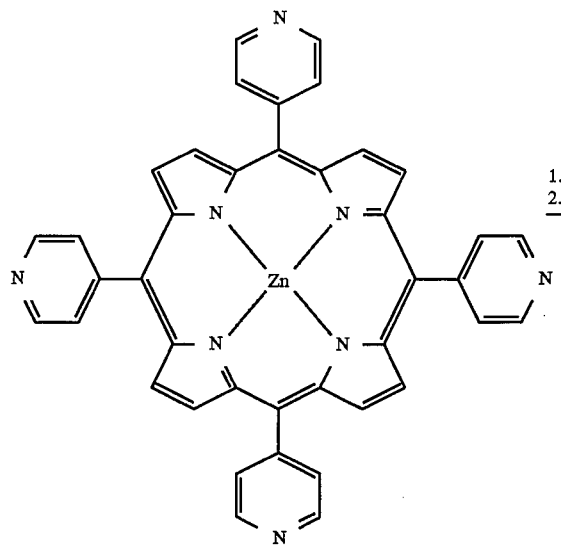
1. OsO₄
2. H₂S →
46
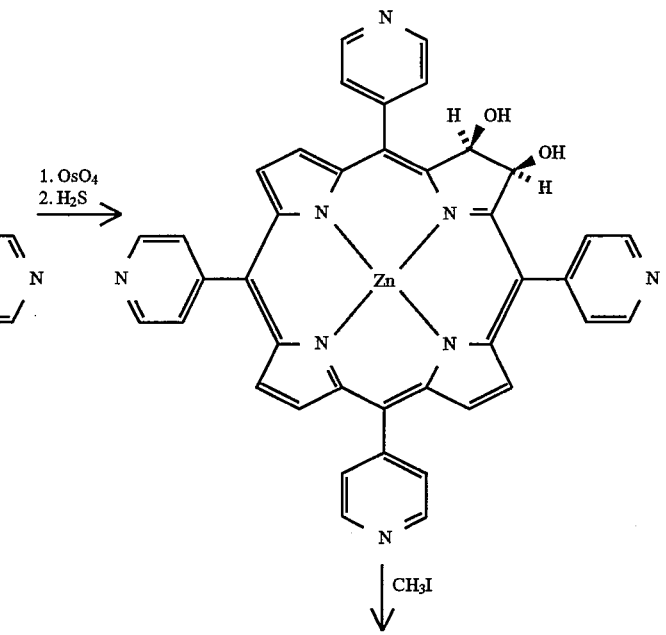
↓ CH₃I
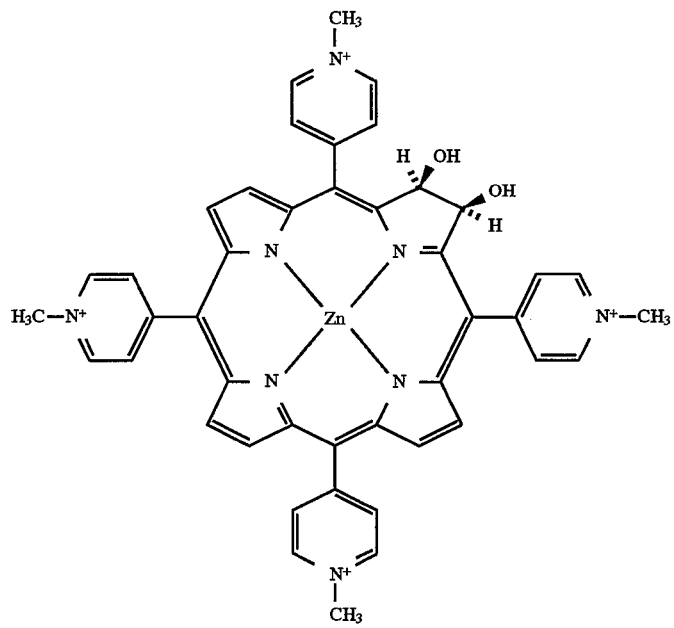
The product compound of Example 3 was prepared analogously to the general procedure of Example 2:
$R_f$=0.12 (silica gel, $CH_2Cl_2$/10.0% MeOH/2.0% pyridine);
UV-Vis($CH_2Cl_2$): $\lambda_{max}$=408 (sh), 424 (Soret), 526, 570, 598, 629 nm;
MS (+FAB, thioglycerol) m/e (%): 715 (56, M⁺+H) , 697 (27, M⁺+H-H₂O);
MS (+FAB, thioglycerol) calc'd for $C_{40}H_{26}N_8O_2Zn$: 714.14702, found: 714.15401.
Example 4: Preparation of cis-2,3-Dihydroxy-5,10,15,20-tetraphenylbacteriochlorin

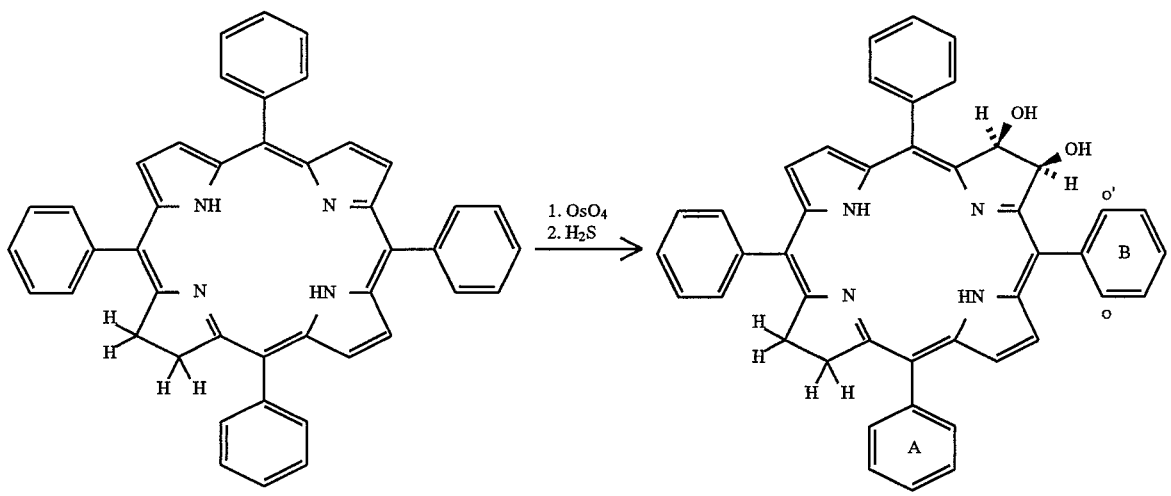

The compound above was prepared according to the general procedure of Example 1. Thus, tetraphenylporphyrin was oxidized with 1.22 equivalents of $OsO_4$ over a two-day period. The oxidation reaction was quenched with $H_2S$, and the product was chromatographically purified. Yield: 53%:

$R_f$=0.78 (silica gel, 2.5% $MeOH/CH_2Cl_2$);

$^1H$ NMR (400 MHz, $CDCl_3$) δ=−1.58 (s, 2H, NH); 3.00 (s, 2H, OH); 3.94–4.21 (m, 4H, pyrrolin-2, 3-H); 6.13 (s, 2H, pyrrolin-12, 13-H); 7.58–7.73 (m, 12H, phenyl$^{A,B}$-(m,p)-H); 7.79 (br tr, J=6.8Hz, 4H, phenyl$^A$-o-H); 7.86 (br d, J=4.4Hz, 2H, phenyl$^B$-o-H); 7.97 (dd, J=4.8, 2Hz, 2H, phenyl$^B$-o-H); 8.13 (2 overlapping d-2nd order, 4H, (β',β") -H);

UV-Vis ($CH_2Cl_2$-0.5% MeOH): λ[nm] (log ε) 378 (4.96), 524 (4.49), 724 (4.71);

LR-MS (+FAB, 3-NBA) m/e(%): (100, $M^+$), 633 (19.2, $M^+$-OH).

HR-MS (+FAB, 3-NBA): calc'd for $C_{44}H_{34}N_4O_2$: 650.26818; found 650.27118.

Example 5: Preparation of the Two Isomeric Tetrahydroxytetraphenylbacteriochlorins, 2R,3S,12R, 13S-Tetrahydroxy-5,10,15,20-tetra phenylbacteriochlorin and 2R,3S,12S,12R-Tetrahydroxy-5,10,15,20-tetraphenylbacteriochlorin

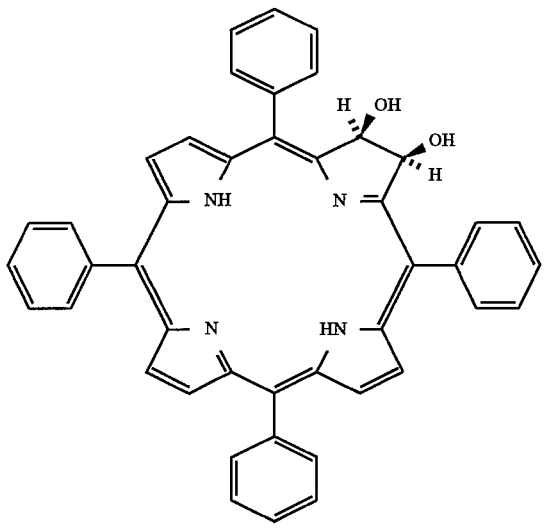

1. 1 equ. $OsO_4$
2. Reduction

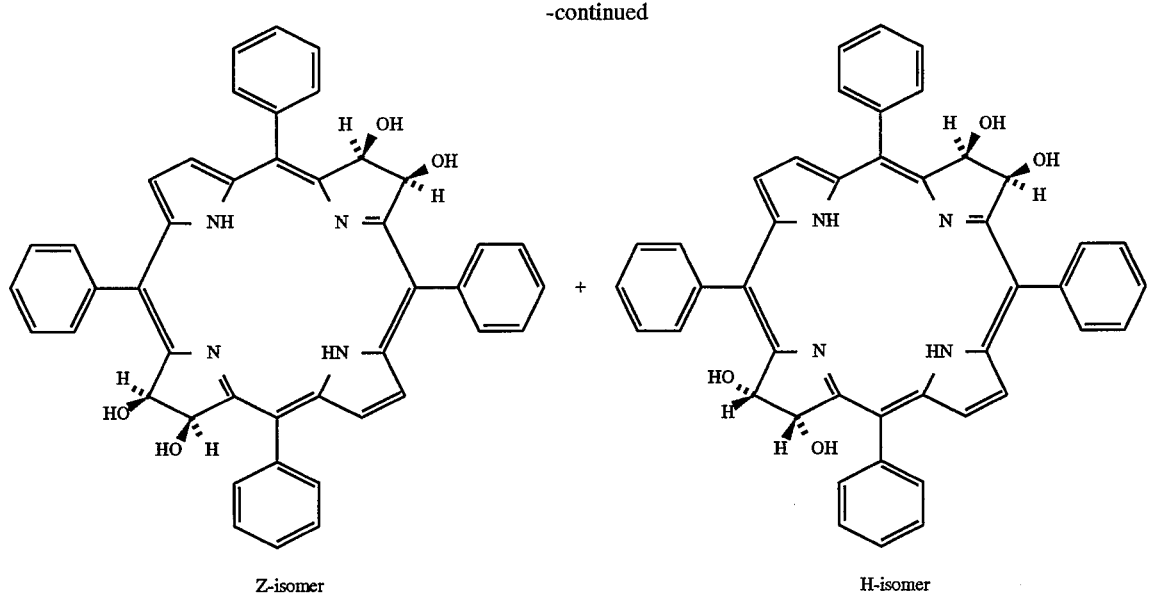

Z-isomer       H-isomer 100 mg of the starting compound above ($1.54 \times 10^{-4}$) were dissolved in a minimal amount of $CHCl_3$ containing 10% pyridine (ca. 4 ml). 51 mg $OsO_4$ (1.3 equivalents) were added, and the stoppered solution was stirred at room temperature until the chlorin peak at 644 nm was largely replaced by the bacteriochlorin peak at 708 nm (16 hours). The oxidation reaction was quenched by bubbling gaseous $H_2S$ through the reaction mixture. After filtering the solution to remove the resulting precipitate, the solvent was removed from the filtrate by evaporation. The resulting mixture was separated on a prepared TLC plate (silica gel, 2 mm, 5% MeOH in $CH_2Cl_2$ as eluent, two developments). The purplish starting compound moved more quickly, almost simultaneously with the solvent front, while the dark pink bacteriochlorins followed with:

E-isomer: $R_f$(silica gel, 5% MeOH in $CH_2Cl_2$)=0.51
Z-isomer: $R_f$(silica gel, 5% MeOH in $CH_2Cl_2$)=0.30
After isolation and recrystallization in $CH_2Cl_2$/hexane, the combined yields were 40%. The two isomers occurred in a 1:1 ratio (21 mg of each).

Because the symmetry groups of the two isomers, $C_{2v}$ and $C_{2h}$, respectively, did not allow distinction based on NMR, UV-Vis, or MS, tentative assignment of the E-isomer or the Z-isomer structure to the individual bacteriochlorins was made based on their chromatographic behavior. The compound with both sets of hydroxy functionalities on the same side of the porphyrin plane ('Z-relationship') was assumed to be more polar than where the two sets of hydroxy functionalities have an 'E-relationship'.
E-isomer:

$R_f$=0.51 (silica gel, $CH_2Cl_2$/5.0% MeOH);
$^1H$ NMR (300 MHz, DMSO-$d_6$): δ=−1.65 (s, 2H, NH); 4.99 (d, J=4.9Hz, 4H, OH); 5.87 (d, J=4.9Hz, 4H, pyrrolidin-H); 7.6 (br m, 12H, phenyl m-, p-H); 7.86 (br(s), 4H, β-H); 7.96 (d, J=1.8Hz, 8H, phenyl-o-H);
$^{13}C$ NMR (75 MHz, DMSO-$d_6$): δ=73.112, 115.631, 122.879, 127.100, 131.537, 133.852, 136.223, 141.217, 160.067;
UV-Vis ($CH_2Cl_2$-0.5% MeOH): λ[nm] (log ε) 376 (5.42), 528 (5.08), 708 (4.89);
LR-MS (+FAB, 3-NBA) m/e (%): 682 (100, $M^+$), 665 (31.1, $M^+$ -OH), 648 (5.8, $M^+$ -2OH), 613 (6.4, $M^+$ -4OH -H);
HR-MS (+FAB, 3-NBA) calc'd for $C_{44}H_{34}N_4O_4$: 682.258??, found 682.25470.
Z-isomer:
$R_f$=0.30 (silica gel, $CH_2Cl_2$/5.0% MeOH);
$^1H$ NMR (400 MHz, DMSO-$d_6$): δ=−1.75 (s, 2H, NH); 5.05 (br s, 4H, OH); 5.95 (s, 4H, pyrrolidine-H); 7.65 (br s, 12H, phenyl-p,-m-H); 7.93 (br s, 4H, β-H); 8.09 (s, 8H, phenyl-o-H);
UV-Vis ($CH_2Cl_2$-0.5% MeOH): λ[nm] (log ε) 376 (5.42), 528 (5.08), 708 (4.89);
LR-MS (+FAB, 3-NBA) m/e (%): 682 (19.4, $M^+$); 665 (7.4, $M^+$ -OH); 649 (9.4); 648 (7.5, $M^+$ -2OH); 613 (1.5, $M^+$ -4OH -H).
HR-MS (+FAB, 3-NBA) calc'd for $C_{44}H_{34}N_4O_4$: 682.25797, found: 682.25518;
Example 6: Pinacol-Type Rearrangement to Form β-oxo-tetraphenylporphyrin (Cpd. 3) and B-oxo-tetraphenylmetalloporphyrin (Zn-3)

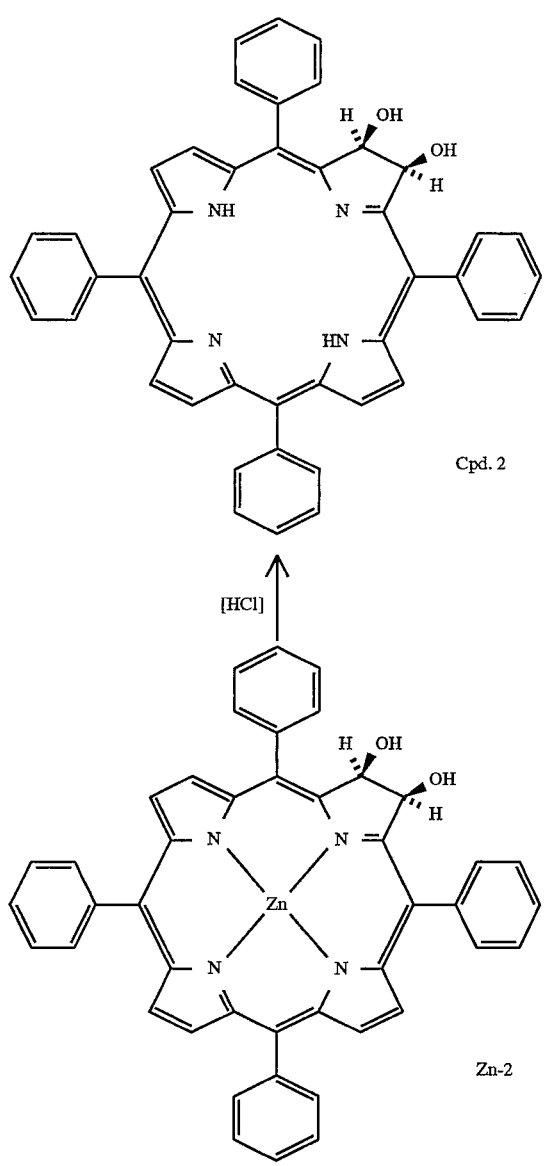

Cpd. 2

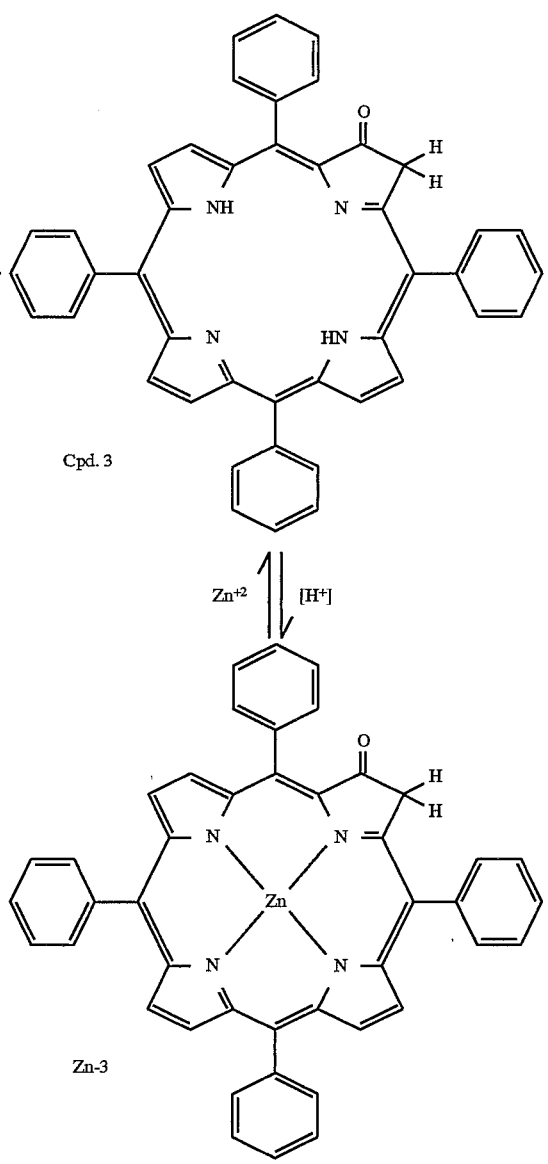

Cpd. 3

Zn-2

Zn-3

Cpd. 3: 2,oxy-5,10,15,20-tetraphenylporphyrin 100 mg (1.54×10⁻⁴ mol) of the starting material, 3,4-dihydroxy-5,10,15,20-tetraphenylchlorin (Cpd. 2), were dissolved in 10 ml $CH_2Cl_2$, and 3 drops of $HClO_4$ (70% aqueous solution) were added. The mixture was refluxed for three minutes. Completion of the reaction was indicated by a sharp peak at 520 nm in the UV-visible spectrum of an aliquot neutralized with $Et_3N$ after about three minutes. The resulting bright green mixture was cooled, washed with aqueous $NH_3$, dried over anhydrous $Na_2SO_4$, evaporated to dryness, and chromatographed on silica (10 g, 280–400 mesh) with $CH_2Cl_2$ as an eluent. The product, Cpd. 3, was crystallized from $CH_2Cl_2$/hexane. Yield: 92 mg (95%).

Alternatively, the zinc chlorin Zn-2 was used as a starting compound. Under the dehydration conditions (refluxing $CHCl_3$ with a drop of concentrated $HClO_4$), the product was demetallated, yielding Cpd. 3. Less acid-labile complexes of Cpd. 2, like Ni-2 or Cu-2, were dehydrated under these conditions without concomitant demetallation. Under less harsh conditions ($CHCl_3$ containing a drop of concentrated HCl at room temperature), Zn-2 was demetallated without dehydration.

Zn-3: (2-oxy-5,10,15,20-tetraphenyl-porphyrinato) zinc(II)

Cpd. 3 was metallated with Zn(II)-acetate in pyridine/$CHCl_3$ to form Zn-3.

The β-oxoporphyrin, Cpd. 3, and the β-oxometalloporphyrin, Zn-3, proved to be identical with the compounds described by Crossley, et al. *J. Org. Chem.* 53:1132–37 (1988).

Example 7: Isopropylidene Acetal

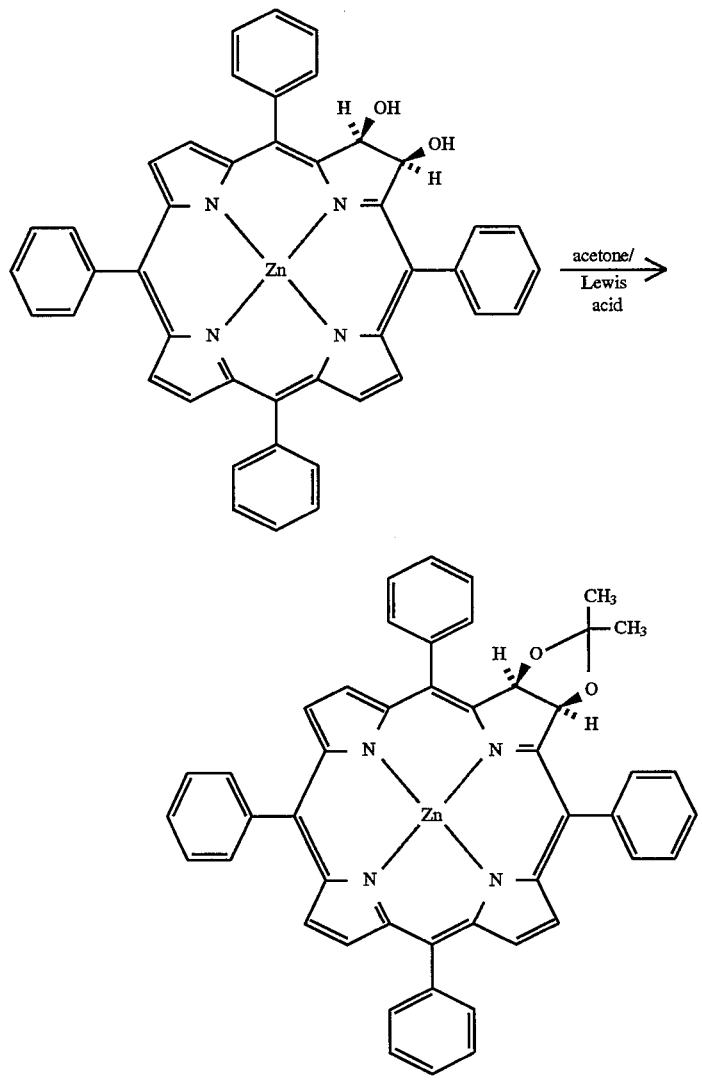

20 mg of [2,3-vic-dihydroxy-tetraphenylporphyrinato]Zn (II) were refluxed for 20 minutes in 10 ml of dry acetone with 100 mg of freshly fused $ZnCl_2$. Evaporation to dryness and column chromatography (silica gel/$CH_2Cl_2$) yielded 12.5 mg (60%) [(2,3-di-O-isopropylidene)-5,10,15,20-tetraphenylchlorinato]zinc(II).

$^1$H NMR (300 MHz, $CDCl_3$) δ=0.61 (s, 3H, $CH_3$-a); 1.37 (s, 3H, $CH_3$-b); 6.46 (s, 2H, pyrroline-H); 7.55–7.76 (m, 12H, phenylA,B-(m,p)-H); 8.05 (dd, J=8.0, 2.1Hz, 4H, phenyl-o); 8.12 (hidden m, 4H, phenyl-o); 8.16 (d, J=6.0Hz, 4H, β"-H); 8.41 (s, 2H, β-H); 8.53 (d, J=6.0Hz, 2H, β'-H);

UV-Vis ($CH_2Cl_2$): λ=418 (Soret), 520, 564, 594 (sh), 612 nm;

LR-MS (+FAB, 3-NBA) m/e(%)=750 (11,$M^+$); 693 (23, $M^+$-C3H6O);

HR-MS (+FAB, 3-NBA)) m/e calc'd for $C_{47}H_{34}N_4O_2Zn$: 750.19732, found 750.19422.

We claim:

1. A β,β'-dihydroxy meso-substituted chlorin, bacteriochlorin or isobacteriochlorin compound having the formula (I) or (II):

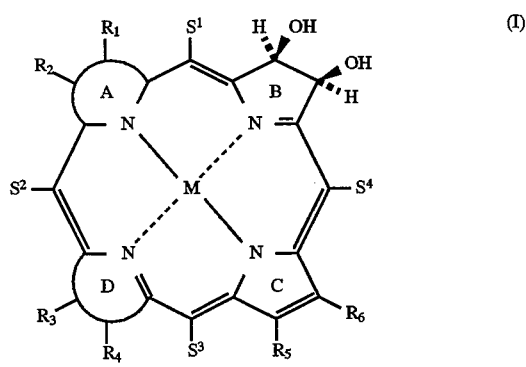

or

-continued

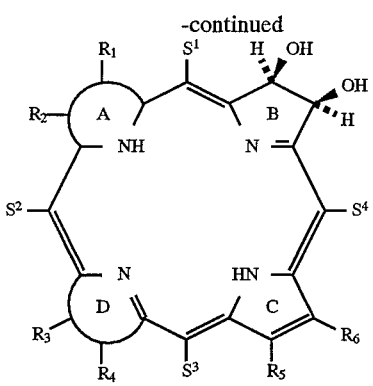

(II)

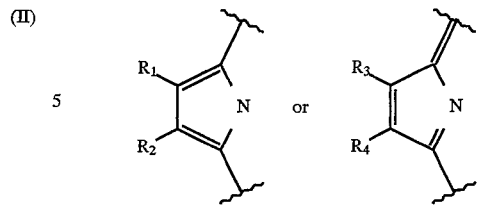

wherein M is a metal selected from the group consisting of Ni(II), Cu(II), Zn, Sn, Ge, Si, Ga, Al, Mn(III), Gd(III), In and Tc;

A is a ring having the structure:

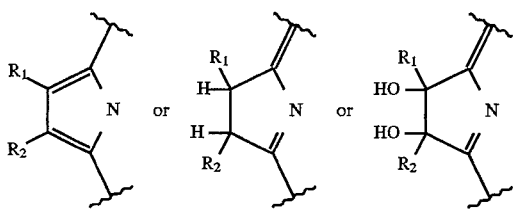

D is a ring having the structure:

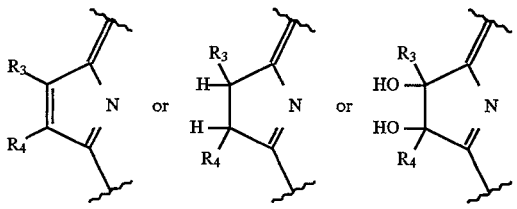

$R_1$ through $R_6$ are independently a hydrogen atom, a lower alkyl group, a lower alkyl carboxylic acid or acid ester group, keto, hydroxy, nitro, amino, or a group that, taken together with another ring, ring substituent or meso-substituent, forms a fused 5- or 6-membered ring; and $S^1$ through $S^4$ are H, substituted or unsubstituted alkyl groups, substituted or unsubstituted cycloalkyl groups, or substituted or unsubstituted aromatic rings, which may be the same or different, with the proviso that at least one of $S^1$ through $S^4$ is not H.

2. The compound of claim 1 having the formula (I) wherein M is Zn.

3. The compound of claim 1 having the formula (II).

4. The compound of claim 1 wherein at least one of A and D is a ring having the structure:

5. The compound of claim 1 wherein $R_1$ through $R_6$ are independently hydrogen, methyl, ethyl, or lower alkyl esters.

6. The compound of claim 1 wherein $S^1$ through $S^4$ are selected from the group consisting of phenyl, naphthyl, pyridinyl, and lower N-alkyl pyridinium salts.

7. The compound of claim 1 wherein at least one of $S^1$ through $S^4$ has the structure:

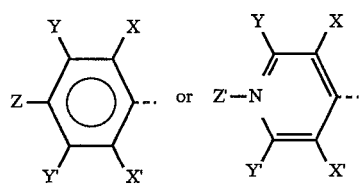

wherein X, X', Y, Y' and Z are independently hydrogen, halogen, lower alkyl, lower alkoxy, hydroxy, carboxylic acid or acid salt, carboxylic acid ester, sulfonic acid or acid salt, sulfonic acid ester, substituted or unsubstituted amino, cyano, nitro, or a biologically active group, and Z' is hydrogen or lower alkyl.

8. The compound of claim 7 wherein X, X', Y, Y' and Z are selected from the group consisting of hydrogen, methyl, ethyl, t-butyl, methoxy, hydroxy, and OR, where R is an alkyl group or a fatty acid group having from 6 to 18 carbon atoms, fluoro, chloro, iodo, bromo, —C(O)-OCH$_3$, cyano or nitro.

9. The compound of claim 7 wherein X, X', Y and Y' are each hydrogen and Z is selected form the group consisting of hydrogen, halogen, lower alkyl, lower alkoxy, hydroxy, carboxylic acid or acid salt, carboxylic acid ester, sulfonic acid ester, sulfonic acid or acid salt, nitro, amino and cyano.

10. The compound of claim 7 wherein at least one of X, X', Y, Y' and Z is a substituent that increases the amphiphilic nature of the molecule.

11. The compound of claim 1 wherein each of $S^1$ through $S^4$ is selected from the group consisting of phenyl, pyridinyl, and lower N-alkyl pyridinium salts.

12. The compound of claim 11 wherein $S^1$ through $S^4$ are identical.

* * * * *